United States Patent [19]
Lowe et al.

[11] Patent Number: 6,117,996
[45] Date of Patent: Sep. 12, 2000

[54] TRIAZINE BASED LIGANDS AND USE THEREOF

[75] Inventors: Christopher Robin Lowe, Saffron Walden; Kenneth Sproule; Rongxiu Li, both of Cambridge, all of United Kingdom; David Johnson Stewart, Huntingdon, N.Y.; James Christopher Pearson; Steven James Burton, both of Cambridge, United Kingdom

[73] Assignee: Novo Nordisk A/S, Bagsvaerd, Denmark

[21] Appl. No.: 09/071,927

[22] Filed: May 1, 1998

Related U.S. Application Data

[63] Continuation-in-part of application No. 08/849,502, Jun. 5, 1997, abandoned, which is a continuation of application No. PCT/DK96/00399, Sep. 19, 1996.

[30] Foreign Application Priority Data

Sep. 20, 1995 [GB] United Kingdom .................. 9519197
Mar. 20, 1998 [DK] Denmark ................................ 0399/98

[51] Int. Cl.$^7$ .................................................. C07D 251/02
[52] U.S. Cl. ........................ 544/216; 544/215; 210/198.2
[58] Field of Search .................................. 544/215, 216; 210/198.2

[56] References Cited

FOREIGN PATENT DOCUMENTS

0302503 A2  2/1989  European Pat. Off. .

OTHER PUBLICATIONS

Atkinson et al., Affinity Chromatography and related techniques, 1982, Elsevier.

Konieczny, M. et al., Arch Immunol. Ther. Exp., vol. 30, No. 1, pp. 1–9 (1982).

Burton, N.P. et al., J. Mol. Recogn., vol. 5, pp. 55–68 (1992).

Burton, S.J. et al., J. Chrom., vol. 508, pp. 109–125, (1990).

Atkinson, A. et al., "The Potential of Organic Dyes as Affinity Ligands in Protein Studies", In:Affinity Chromatography and Related Techniques, Proc. 4th Int. Symp. Edited by T.C.J. Gribnau et al., Elsevier Sci. Publ., Amsterdam, Anal. Chem. Symp. Series, 1982, vol. 9, pp. 399–410.

*Primary Examiner*—Mukund J. Shah
*Assistant Examiner*—Pavanaram K. Sripada
*Attorney, Agent, or Firm*—Steve T. Zelson; Carol E. Rozek

[57] ABSTRACT

The present invention relates to novel affinity ligand-matrix conjugates comprising a ligand with the general formula (a)

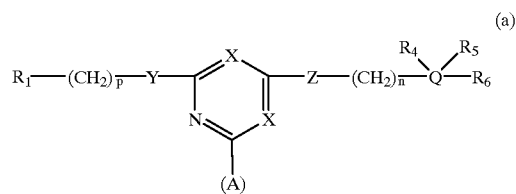

which ligand is attached to a support matrix in position (A), optionally through a spacer arm interposed between the matrix and ligand. The invention furthermore relates to these novel affinity ligand-matrix conjugates and the preparation and use thereof in the purification of proteinaceous materials such as e.g. immunoglobulins, insulins, Factor VII, or human Growth Hormone or analogues, derivatives and fragments thereof and precursors.

36 Claims, No Drawings

TRIAZINE BASED LIGANDS AND USE THEREOF

CROSS-REFERENCE TO RELATED APPLICATIONS

This application is a continuation-in-part of application Ser. No. 08/849,502 filed on Jun. 5, 1997 which claims the benefit of application Ser. No. PCT/DK96/00399 filed on Sep. 19, 1996 via the PCT and claims priority under 35 U.S.C. 119 of Great Britain application 9519197.9 filed Sep. 20, 1995, and of Danish application serial no. 0399/98 filed Mar. 20, 1998, the contents of which are fully incorporated herein by reference. This application is a C.I.P. of 08/849,502 filed Jun. 5, 1997 abandoned which is a continuation of PCT/DK96/00399 filed Sep. 19, 1996.

The present invention relates to novel affinity ligands, their preparation and attachment to matrices which may consist of solid, semi-solid, particulate or colloidal materials, or soluble polymers. The invention furthermore relates to these novel affinity ligand-matrix conjugates and the preparation and use thereof in the purification of proteinaceous materials such as e.g. immunoglobulins, insulins, Factor VII, or Human Growth Hormone or analogues, derivatives and fragments thereof and precursors.

BACKGROUND OF THE INVENTION

Modern protein purification principles very much rely upon chromatographic separation techniques such as gel permeation chromatography (GPC), ionexchange chromatography (IEC), hydrophobic interaction chromatography (HIC), reversed phase high pressure chromatography (RP-HPLC), and affinity chromatography (AC). These techniques are easily adapted to laboratory scale purification of peptides and proteins meant for research and scientific experiments, resulting in pure and biologically active substances. In most cases little or no interest is paid to process economy, process validation, or cleaning in place procedures, as the material will only rarely be used for clinical experiments and because labour costs far exceed the costs of equipment and matrices.

However, large scale industrial downstream processing must take into consideration factors such as economy, robustness of matrices and cleaning in place with e.g. NaOH, urea, or ethanol. Today the demand for inexpensive and robust matrices stable in 1 M NaOH, 7M urea, or 80% v/v ethanol is met by a number of commercial suppliers within the field of GPC, IEC, HIC, and RP-HPLC. A combination of these principles has for many years resulted in almost pure protein bulk substances although use of extreme buffers and many purification steps have resulted in poor recoveries, increased costs and questionable stability of the bulk preparations.

It has long been realised that the principle of affinity chromatography could also be applied to large scale operations. Unfortunately, adsorbents created with natural biological ligands such as monoclonal or polyclonal antibodies tend to be expensive to produce because the ligands themselves often require extensive purification, are biologically and chemically labile and tend to be difficult to immobilise with retention of their biological activity. Therefore, there has been a long term need to replace the expensive chemically and biologically labile monoclonal or polyclonal antibodies with less expensive and more robust ligands mimicking the specificity of antibodies.

Affinity chromatography occupies a unique place in separation technology as the protein to be purified adsorbs selectively and reversibly to the complementary binding substance such as an antibody molecule. Purification factors of several thousandfold are often observed with high recoveries, in contrast to the conventional purification methods offering factors from 5–50 times. The high purification factors obtained in affinity chromatography dramatically reduces the number of purification steps in the downstream process. Further, the very low non specific binding observed in affinity chromatography, makes it possible to purify a given protein from complex biological mixtures, to separate incorrectly folded forms from native molecules, and to recover the protein specifically from even large volumes of tissue extracts or fermentation cultures.

The affinity sorbent comprises a solid, usually permeable, support matrix, to which a suitable ligand is covalently attached, contained in a conventional chromatographic column. A crude sample, containing the complementary biopolymer is passed over the support matrix, under conditions which promote specific binding interactions with the immobilised ligand. The column is washed with buffer to remove unretarded molecules followed by an elution step in which the protein is eluted in its pure form. A typical affinity adsorbent is based on a solid support, a spacer arm and a ligand. The solid support can be made of bead-formed agarose with an open pore structure. The spacer arm may encourage protein binding by making the ligand more accessible. The length and nature of the spacer arm can be determined by a person skilled in the art. The ligand should exhibit specific and reversible binding to the protein to be purified even after immobilization. In addition to antibodies, a number of compounds including enzymatic co-factors, amino acids, peptides, proteins, concanavalin A, Lectin, thiols, and dyes have been used as affinity ligands.

Affinity chromatography has been used in many applications. A comprehensive list is given in e.g. "Affinity Chromatography A Practical Approach" from IRL Press, 1985, and "Affinity Chromatography, Principles and Methods" from Pharmacia Fine Chemicals 1979.

Conventional substrate or substrate analogue affinity ligands, especially dyes, have been used for large scale purification of specific enzymes or groups of enzymes. (Scawen M. D. and Atkinson T. 1987, Reactive Dyes in Protein and Enzyme Technology, Ed. Clonis Y. D. et al; Macmillan Press, pp. 51–85).

Dye affinity chromatography has over the years gained much interest because of the relative low price of such matrices, their robustness and their ability to withstand NaOH, urea and ethanol. Some of the more widely used ligands in this type of affinity chromatography have been a variety of reactive triazine-based textile dyes immobilised to agarose and other supports. The use of affinity chromatography on immobilized dyes has been reviewed (Lowe C. R. and Pearson J. C. 1984, Methods in Enzymology 104, pp. 97–113). Selective interactions with the $NAD^+$-binding site of horse liver alcohol dehydrogenase were shown with dye analogues of Cibacron Blue F3G-A (Lowe C. R. et al 1986; Journal of Chromatography 376, pp. 121–130). The selective purification approach was further illustrated with the computer aided design of a novel affinity adsorbent mimicking the phenyl-arginine dipeptide substrate for the purification of porcine pancreatic kallikrein (Burton N. P. and Lowe C. R. 1992, Journal of Molecular Recognition 5, pp. 55–58).

U.S. Pat. No. 4,562,251 discloses a particular ligand structure consisting of two m-aminophenyl boronic acid groups attached to a triazine ring for glycoprotein separation.

However, despite the rapid progress in affinity technology over the past few years, the need is still to develop a technology by which a specific mimetic ligand can be identified for a protein in order to produce an inexpensive and stable affinity column capable of repeated large scale purification of the said protein, e.g. in the separation and purification of proteinaceous materials, such as immunoglobulins, insulins, Factor VII, or human Growth Hormone or analogues, derivatives and fragments thereof and precursors, whether derived from natural or recombinant sources.

DETAILED DESCRIPTION OF THE INVENTION

The present invention relates to novel affinity ligands, their preparation and attachment to matrices, and the use of these novel affinity ligand-matrices in the purification of proteinaceous materials.

The current invention is based on the notion that the selectivity of hydrophobic ligands may be increased by increasing the complexity and spatial geometry of the hydrophobic component, and the incorporation of various functional groups capable of partaking in electrostatic and hydrogen bonding interactions thereby promoting selective interactions with protein binding sites. This work led to the discovery of a generic group of novel affinity ligands, which have been unexpectedly found to be generally applicable to the isolation and purification of proteins by affinity chromatography.

In contrast to the above mentioned selective approach where enzyme substrates, analogues thereof or substrate mimetics were used as ligands, the ligands defined in this application are directed towards any surface of the protein molecule, making the principle applicable for any protein. The ligands are designed by computer modelling techniques and/or by screening of mimetic ligand libraries. Further, the current invention has the advantage that the structure of the protein binding site architecture is not required for design and development of the ligand, and consequently the materials and techniques described herein have a significantly greater utility.

A feature of the present invention is the provision of a general tool for protein resolution, isolation and purification. A family of subtly different chemical structures has been synthesised, which have the ability to interact with different proteins. A particularly effective ligand structure for a given protein is identified by screening a range of ligands provided by the invention for suitable binding properties.

By way of example, affinity ligands of high selectivity and specificity which are currently available for the separation and purification of immunoglobulins are often proteinaceous materials derived from either bacterial or recombinant sources and include materials such as Protein A, Protein G and Protein L. Immobilisation of these, and similar, proteins often results in a significant loss of biological activity. Continual and repeated use of immobilised proteins as affinity media leads to a further diminution of biological activity. Furthermore, the inherent nature of these biological macromolecules imposes strict limitations with respect to the use of buffer salts, organic solvents and pH levels in affinity chromatography and related techniques.

Novel affinity ligands provided by this invention can be used in place of protein A and Protein G and are significantly more flexible in their use, are more robust, less expensive to produce and offer equivalent levels of purification.

Another example is the use of novel affinity matrices provided by this invention in biotechnology.

The present invention relates to affinity ligand matrix conjugates comprising a ligand with the general formula (a):

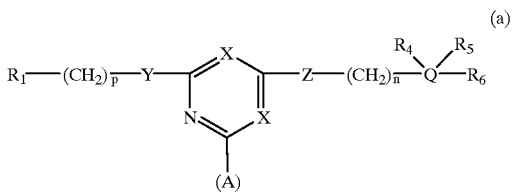

(a)

wherein $R_1$ represents a hydrogen atom, an alkyl group containing from 1 to 6 carbon atoms, a hydroxyalkyl group containing from 1 to 6 carbon atoms, a cyclohexyl group, an amino group, a phenyl group, naphthyl group, 1-phenylpyrazole, indazole, benzthiazole group, benzoxazole group, or a benzimidazole group, each of which benzene, naphthalene, phenylpyrazole, indazole, benzthiazole, benzoxazole or benzimidazole ring is optionally substituted with one or more substituents independently selected from the group consisting of alkyl groups containing from 1 to 6 carbon atoms, alkoxy groups containing from 1 to 6 carbon atoms, acyloxy or acylamino groups containing from 1 to 6 carbon atoms, amino groups, hydroxyl groups, carboxylic acid groups, sulphonic acid groups, carbamoyl groups, sulphamoyl groups, alkylsulphonyl groups containing from 1 to 6 carbon atoms or halogen atoms;

Y represents an oxygen atom, a sulphur atom or a group N—$R_2$;

Z represents an oxygen atom, a sulphur atom or a group N—$R_3$;

$R_2$ and $R_3$ each independently represent a hydrogen atom, an alkyl group containing from 1 to 6 carbon atoms; a hydroxyalkyl group containing from 1 to 6 carbon atoms, a benzyl group or a β-phenylethyl group;

$R_4$, $R_5$ and $R_6$ each independently represent a hydrogen atom, a hydroxyl group, an alkyl group containing from 1 to 6 carbon atoms, an alkoxy group containing from 1 to 6 carbon atoms, an amino group, an acyloxy or acylamino group containing from 1 to 6 carbon atoms, a carboxylic acid group, a sulphonic acid group, a carbamoyl or sulphamoyl group, an alkylsulphonyl group containing from 1 to 6 carbon atoms or a halogen atom;

one of the symbols X represents a nitrogen atom and the other symbol X represents a nitrogen atom or a carbon atom carrying a chlorine atom or a cyano group;

Q represents a benzene, naphthalene, benzthiazole, benzoxazole 1-phenylpyrazole, indazole or benzimidazole ring;

n is an integer between 0 and 6;

p is an integer between 0 and 20; and which ligand is attached to a support matrix in position A, optionally through a spacer arm interposed between the matrix and ligand.

The optional spacer arm is preferably represented by the general formula (b)

—T—[—L—V—]$_m$— (b)

wherein T represents an oxygen atom, a sulphur atom or a group N—$R_7$;

wherein $R_7$ represents a hydrogen atom or an alkyl group containing from 1 to 6 carbon atoms;

V represents an an oxygen atom, a sulphur atom, a —COO— group, a CONH group or an NHCO group or a —PO$_3$H— group, an NH-arylene-SO$_2$—CH$_2$—CH$_2$ group or an N—$R_8$ group; wherein $R_8$ represents a hydrogen atom or an alkyl group containing from 1 to 6 carbon atoms;

L represents an optionally substituted hydrocarbon linkage containing from 2 to 20 carbon atoms; and m is 0 or 1.

The support matrix may be any compound or material, particulate or non particulate, soluble or insoluble, porous or non porous which may be used in conjunction with affinity ligands to form a affinity ligand matrix conjugate and which provides a convenient means of separating the affinity ligands from solutes in a contacting solution.

The present invention provides novel affinity ligand-matrix conjugates, which affinity ligand-matrix conjugates may be used in the separation and purification of proteinaceous materials, such as immunoglobulins, insulins, Factor VII, or human Growth Hormone or analogues, derivatives and fragments thereof and precursors, whether derived from natural or recombinant sources.

In a preferred embodiment, the invention provides novel affinity ligand matrix conjugates which are represented by the General Formula (I):

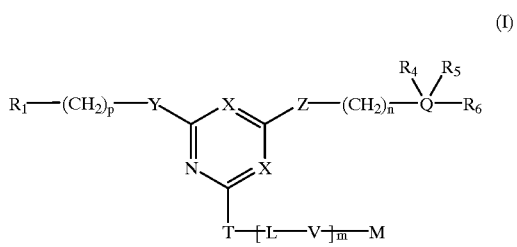

wherein $R_1$, Y, Z, $R_2$, $R_3$, $R_4$, $R_5$, $R_6$, X, Q, n and p have the meanings specified above, T represents an oxygen atom, a sulphur atom or a group N—$R_7$;

V represents an oxygen atom, a sulphur atom, a —COO— group, a CONH group or an NHCO group or a —$PO_3H$— group, an NH-arylene-$SO_2$—$CH_2$—$CH_2$ group or an N—$R_8$ group;

$R_7$ and $R_8$ each independently represents a hydrogen atom or an alkyl group containing from 1 to 6 carbon atoms;

L represents an optionally substituted hydrocarbon linkage containing from 2 to 20 carbon atoms;

m is 0 or 1; and

M represents the residue of a support matrix.

The term "alkyl group containing from 1 to 6 carbon atoms" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl and 2,2-dimethylpropyl.

The term "hydroxyalkyl group containing from 1 to 6 carbon atoms" as used herein, alone or in combination, refers to a straight or branched, saturated hydrocarbon chain having 1 to 6 carbon atoms substituted with one or more hydroxy groups, preferably one hydroxy group, such as e.g. hydroxymethyl, 2-hydroxyethyl, 3-hydroxypropyl, 2-hydroxypropyl, 4-hydroxybutyl, 5-hydroxypentyl, 6-hydroxyhexyl.

The term "alkoxy group containing from 1 to 6 carbon atoms" as used herein, alone or in combination, refers to a straight or branched monovalent substituent comprising an alkyl group containing from 1 to 6 carbon atoms linked through an ether oxygen having its free valence bond from the ether oxygen and having 1 to 6 carbon atoms e.g. methoxy, ethoxy, propoxy, isopropoxy, butoxy, pentoxy.

Term "halogen" means fluorine, chlorine, bromine or iodine.

The term "acyloxy or acylamino containing from 1 to 6 carbon atoms" as used herein refers to a monovalent substituent comprising an alkyl group containing from 1 to 5 carbon atoms linked through a carbonyloxy or oxycarbonyl group such as a methylcarbonyloxy, ethylcarbonyloxy, methyloxycarbonyl or ethyloxycarbonyl group or linked through a carbonylamino or aminocarbonyl group such as a methylcarbonylamino, ethylcarbonylamino, methylaminocarbonyl or ethylaminocarbonyl group.

The term "alkylsulfonyl containing from 1 to 6 carbon atoms" as used herein refers to a monovalent substituent comprising a alkyl group containing from 1 to 6 carbon atoms linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "one or more substituents independently selected from" shall more preferably refer to from 1–3 substituents. The term shall further preferably refer to 1–2 substituents and most preferably refer to one substituent.

In the present specification, whenever the term insulin is used in a plural or a generic sense, it is intended to encompass both naturally occurring insulins and insulin analogues and derivatives thereof and precursors. By the term insulin is thus also meant insulin from any species, e.g. human insulin. By the term "insulin analogue" as used herein is meant human insulin with one or several amino acid substitutions, one or several amino acid deletions, one or several amino acid additions or combinations hereof. The term "insulin derivative" means insulin chemically modified in one or several residues. By "insulin precursor" as used herein is meant any molecule which by enzymatic or chemical conversion results in formation of insulin, insulin fragments, e.g. des-Thr(B30)-insulin, insulin analogues, or insulin derivatives.

The term "optionally substituted hydrocarbon linkage containing from 2 to 20 carbon atoms" as used herein refers to one or more linear or branched alkyl chains, optionally substituted with for example hydroxy or alkoxy groups containing from 1 to 6 carbonatoms, and optionally linked together by amino, ether, thioether, ester, amide or sulphonamide bonds providing a chain containing from 2 to 20 carbon atoms. The construction is preferably flexible. The construction of such optionally substituted hydrocarbon linkages is for example described in Lowe, C. R. and Dean, P. D. G, 1974, Affinity Chromatography, John Wiley & Sons, London, which hereby are incorporated by reference.

In a preferred embodiment, these conjugates are represented by the General Formula (I):

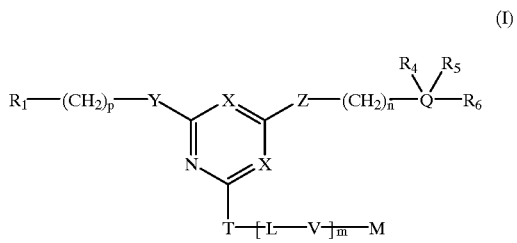

wherein

R$_1$ represents a hydrogen atom, an alkyl group containing from 1 to 6 carbon atoms, a hydroxyalkyl group containing from 1 to 6 carbon atoms, a cyclohexyl group, an amino group, a phenyl group or a naphthyl group, which may be substituted on the benzene or naphthalene ring by alkyl groups containing from 1 to 6 carbon atoms, alkoxy groups containing from 1 to 6 carbon atoms, acyloxy or acylamino groups containing from 1 to 6 carbon atoms, amino groups, hydroxyl groups, carboxylic acid groups, sulphonic acid groups, carbamoyl groups, sulphamoyl groups, alkylsulphonyl groups or halogen atoms;

T represents an oxygen atom, a sulphur atom or a group N—R$_7$;

Y represents an oxygen atom, a sulphur atom or a group N—R$_2$;

Z represents an oxygen atom, a sulphur atom or a group N—R$_3$;

R$_2$ and R$_3$ each independently represent a hydrogen atom, an alkyl group containing from 1 to 6 carbon atoms; a hydroxyalkyl group containing from 1 to 6 carbon atoms, a benzyl group or a β-phenylethyl group;

R$_4$, R$_5$ and R$_6$ each independently represent a hydrogen atom, a hydroxyl group, an alkyl group containing from 1 to 6 carbon atoms, an alkoxy group containing from 1 to 6 carbon atoms, an amino group, an acyloxy or acylamino group containing from 1 to 6 carbon atoms, a carboxylic acid group, a sulphonic acid group, a carbamoyl or sulphamoyl group, an alkylsulphonyl group or a halogen atom;

one of the symbols X represents a nitrogen atom and the other symbol X represents a nitrogen atom or a carbon atom carrying a chlorine atom or a cyano group;

V represents an oxygen atom, a sulphur atom, a —COO— group, a CONH group or an NHCO group or a —PO$_3$H— group, an NH-arylene-SO$_2$—CH$_2$—CH$_2$ group or an N—R$_8$ group;

R$_7$ and R$_8$ each independently represents a hydrogen atom or an alkyl group containing from 1 to 6 carbon atoms;

L represents an optionally substituted hydrocarbon linkage containing from 2 to 20 carbon atoms;

Q represents a benzene or naphthalene ring;

n is an integer between 0 and 6;

p is an integer between 0 and 20;

m is 0 or 1; and

M represents the residue of a support matrix which may be any compound or material, particulate or non particulate, soluble or insoluble, porous or non-porous which may be used in conjunction with affinity ligands to form a novel affinity ligand-matrix conjugate of General Formula (I) and which provides a convenient means of separating the affinity ligands from solutes in a contacting solution.

It will be appreciated that this invention relates, inter alia, to the use of compounds which are pyridines, diazines or triazines carrying a T—[L—V]$_{0-1}$—M substituent, or the precursor thereof, and other substituents linked to the ring via a heteroatom. Such substituents may include any non-interfering group comprising 0 to 10 or 20 C atoms.

In a preferred embodiment of the invention, R$_1$ represents a phenyl or naphthyl group each of which is optionally substituted on the benzene or naphthalene ring with one or more independently selected from the group consisting of hydroxyl groups or carboxylic acid groups.

In another preferred embodiment of the invention, R$_2$ represents a hydrogen atom.

In another preferred embodiment of the invention, R$_3$ represents a hydrogen atom.

In another preferred embodiment of the invention, R$_4$ represents a hydrogen atom, a hydroxyl group, a carboxylic acid group, or an amino group.

In another preferred embodiment of the invention, R$_5$ represents a hydrogen atom, a hydroxyl group, a carboxylic acid group, or an amino group.

In another preferred embodiment of the invention, R$_6$ represents a hydrogen atom, a hydroxyl group, a carboxylic acid group, or an amino group.

In another preferred embodiment of the invention, R$_7$ represents a hydrogen atom.

In another preferred embodiment of the invention, T represents an oxygen atom or an NH group.

In another preferred embodiment of the invention, Y represents N—R$_2$ wherein R$_2$ is as defined above.

In another preferred embodiment of the invention, Z represents N—R$_3$ wherein R$_3$ is as defined above.

In another preferred embodiment of the invention, both X represents a nitrogen atom.

In another preferred embodiment of the invention, Q represents a benzene or naphthalene ring.

In another preferred embodiment of the invention, n represents 0 or 2.

In another preferred embodiment of the invention, p represents 0 or 2.

In another preferred embodiment of the invention, m represents 0 or 1.

In another preferred embodiment of the invention, L represents an ethyl, propyl, hydroxypropyl, butyl, pentyl, hexyl, octyl or decyl group and V and m are as defined above.

In another preferred embodiment of the invention, V represents an oxygen atom, a —COO— group, a —PO$_3$H— group, or an N—R$_8$ group; and more preferred an oxygen atom or an NH group and L and m are as defined above.

In another preferred embodiment of the invention, m represents 1 and L and V are as defined above.

The term "integer between x and y" may include the values x (including zero) and y.

The invention also provides methods for the manufacture of the novel affinity ligand-matrix conjugates according to the invention which comprises reacting, in any order, a halogenoheterocyclic compound of General Formula (II):

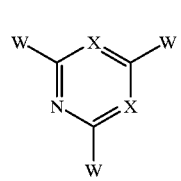

wherein the symbols X have the meaning hereinbefore specified and W represents a halogen atom with (i) a compound of General Formula (III):

$$R_1\text{—}(CH_2)_p\text{—}Y\text{—}H \quad (III)$$

wherein the symbols $R_1$, Y and p have the meanings hereinbefore specified and H is hydrogen, (ii) a compound of General Formula (IV)

$$H\text{—}Z\text{—}(CH_2)_n\text{—}Q\overset{R_4\quad R_5}{\diagdown\diagup}R_6 \quad (IV)$$

wherein the symbols $R_4$, $R_5$, $R_6$, Q, Z and n have the meanings hereinbefore specified, and (iii) with either an optionally derivatised support matrix of General Formula V $$H\text{—}T\text{—}[\text{—}L\text{—}V\text{—}]_m\text{—}M \quad (V)$$

wherein the symbols L, M, V, T, and m have the meanings hereinbefore specified or, with a linking unit of General Formula (VI)

$$H\text{—}T\text{—}L\text{—}V\text{—}H \quad (VI)$$

wherein the symbols H, L, V and T have the meanings hereinbefore specified to give a compound of General Formula (VII):

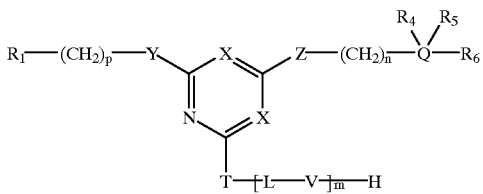

(VII)

wherein $R_1$, $R_4$, $R_5$, $R_6$, Q, L, T, V, X, Y, Z, m, n and p have the meanings hereinbefore specified; the compound of General Formula (VII) is then reacted further with a support matrix whose residue is represented by M using activating and coupling procedures well known to those skilled in the art.

As examples of halogenoheterocyclic compounds of General Formula (II) there may be mentioned 5-chloro-2,4,6-trifluoropyrimidine, 5-cyano-2,4,6-trichloropyrimidine, cyanuric fluoride, cyanuric bromide and, above all, cyanuric chloride.

As examples of compounds of General Formula (III) there may be mentioned amines such as ammonia, methylamine, ethylamine, propylamine, isopropylamine, diisopropylamine, isobutylamine, amylamine, hexylamine, ethanolamine, diethanolamine, aniline, N-methylaniline, N-ethylaniline, N-isopropylaniline, 1,4-diaminobutane, 1,6-diaminohexane, N-tert-butylaniline, p-toluidine, p-butylaniline, 2,4-dimethylaniline, p-anisidine, p-ethoxyaniline, p-aminoacetanilide, p-aminophenol, p-chloroaniline, orthanilic acid, metanilic acid, sulphanilic acid, 4-methylaniline-2-sulphonic acid, 4-methoxyaniline-2-sulphonic acid, aniline-2,5-disulphonic acid, N-methylmetanilic acid, o-, m- and p-aminobenzoic acid, p-aminobenzamide, p-aminobenzenesulphonamide, 1-amino-2-, 3-, 4-, 5-, 6-, 7- and 8-naphthol, 2-amino-3-, 4-, 5-, 6-, 7- and 8-naphthol, 5-, 6- and 7-amino-1-naphthol-3-sulphonic acid, N-benzylaniline, benzylamine, 4-methylbenzylamine, 4-hydroxybenzylamine, 4-methoxybenzylamine, 4-acetoxybenzylamine, 4-acetylaminobenzylamine, N-methylbenzylamine, β-phenylethylamine, N-butyl-benzylamine, N-benzyl-β-phenylethylamine, N-(β-hydroxyethyl)-benzylamine, N-tert-butyl-benzylamine, N-benzyltyramine and tyramine; phenols such as phenol, o-, m- and p-cresol, catechol, resorcinol, hydroquinone, p-chlorophenol, 1-naphthol and 2-naphthol, 1-naphthol-4-sulphonic acid, 2-naphthol-6-sulphonic acid and 2-hydroxy-3-naphthoic acid; thiols such as ethylthiol, thioglycollic acid, thiophenol and thio-p-cresol, and aromatic heterocycles such as 5-amino-1-phenylpyrazole, 6-aminoindazole, 2-aminobenzimidazole, 2-aminobenzthiazole, and 2-amino-5-chlorobenzoxazole.

As examples of compounds of General Formula (IV) there may be mentioned amines such as aniline, N-methylaniline, N-ethylaniline, N-isopropylaniline, N-tert-butylaniline, p-toluidine, p-butylaniline, 2,4-dimethylaniline, p-anisidine, p-ethoxyaniline, p-aminoacetanilide, p-aminophenol, p-chloroaniline, orthanilic acid, metanilic acid, sulphanilic acid, 4-methylaniline-2-sulphonic acid, 4-methoxyaniline-2-sulphonic acid, aniline-2,5-disulphonic acid, N-methylmetanilic acid, o-, m- and p-aminobenzoic acid, 1-amino-2-, 3-, 4-, 5-, 6-, 7- and 8-naphthol, 2-amino-3-, 4-, 5-, 6-, 7- and 8-naphthol, 5-, 6- and 7-amino-1-naphthol-3-sulphonic acid, p-aminobenzamide, p-aminobenzenesulphonamide, N-benzylaniline, benzylamine, 4-methylbenzylamine, 4-hydroxybenzylamine, 4-methoxybenzylamine, 4-acetoxybenzylamine, 4-acetylaminobenzylamine, N-methylbenzylamine, β-phenylethylamine, N-butyl-benzylamine, N-benzyl-β-phenylethylamine, N-(β-hydroxyethyl)-benzylamine, N-tert-butyl-benzylamine, N-benzyltyramine and tyramine; phenols such as phenol, o-, m- and p-cresol, catechol, resorcinol, hydroquinone, p-chlorophenol, 1- and 2-naphthol, 1-naphthol-4-sulphonic acid, 2-naphthol-6-sulphonic acid and 2-hydroxy-3-naphthoic acid; thiols such as thiophenol and thio-p-cresol, and aromatic heterocycles such as 5-amino-1-phenylpyrazole, 6-aminoindazole, 2-aminobenzimidazole, 2-aminobenzthiazole, and 2-amino-5-chlorobenzoxazole.

As examples of support matrices whose residue is represented by M, there may be mentioned insoluble support matrices such as a naturally occurring polymer, for example a polypeptide or protein such as cross linked albumin or a polysaccharide such as agarose, alginate, carrageenan, chitin, cellulose, dextran or starch; synthetic polymers such as polyacrylamide, polystyrene, polyacrolein, polyvinyl alcohol, polymethylacrylate, perfluorocarbon; inorganic compounds such as silica, glass, kieselguhr, alumina, iron oxide or other metal oxides or co-polymers consisting of any combination of two or more of a naturally occurring polymer, synthetic polymer or inorganic compounds. Also included within the definition of support matrices whose residue is represented by M are soluble support matrices comprising polymers such as dextran, polyethylene glycol, polyvinyl alcohol or hydrolysed starch which provide affinity-ligand matrix conjugates for use in liquid partitioning; or support matrices comprising compounds such as perfluorodecalin which provide affinity-ligand matrix conjugates for use in the formation of affinity emulsions. For the avoidance of doubt, a support matrix is defined herein as any compound or material whether particulate or non-particulate, soluble or insoluble, porous or non-porous which may be used to form a novel affinity ligand-matrix conjugate according to the invention and which provides a convenient means of separating the affinity ligand from solutes in a contacting solution.

Also included within the definition of support matrices whose residue is represented by M are support matrices such as agarose, cellulose, dextran, starch, alginate, carrageenan, synthetic polymers, silica, glass and metal oxides which have been, or are, modified by treatment with an activating agent prior to, or during, attachment of the ligand.

In a preferred embodiment of the invention M represents optionally activated agarose, silica, cellulose, glass, toyopearl, hydroxyethylmethacrylate, polyacrylamide, styrenedivinylbenzene, Hyper D, perfluorocarbons.

Preferably M represents optionally tresyl activated, sulphonylchloride activated, tosyl activated, vinylsulphone activated or epoxy activated agarose.

Preferred affinity ligand matrix conjugates according to the invention are i)
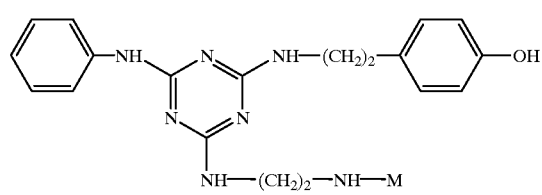

ii)
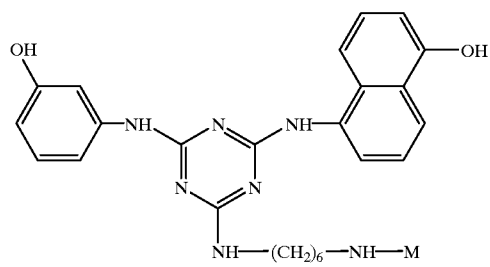

iii)
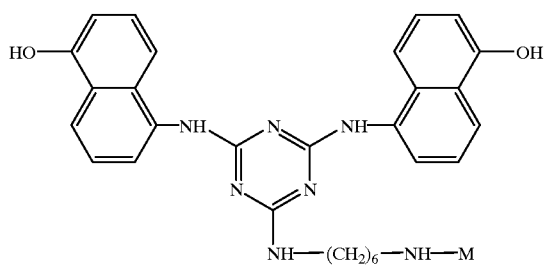

iv)
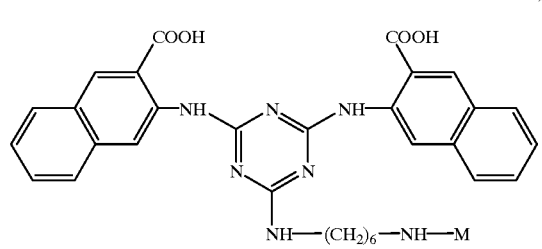

-continued v)
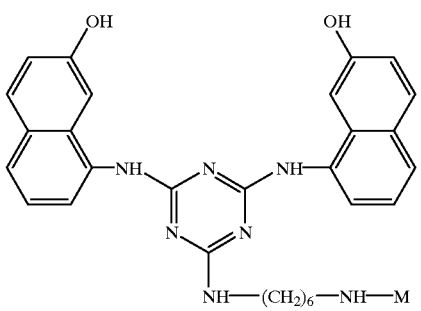

vi)
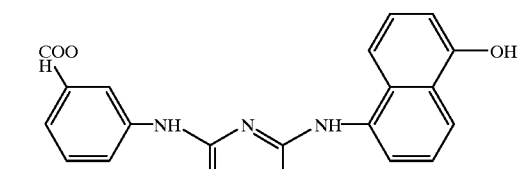

vii)
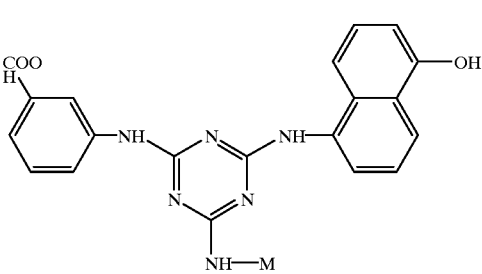

viii)
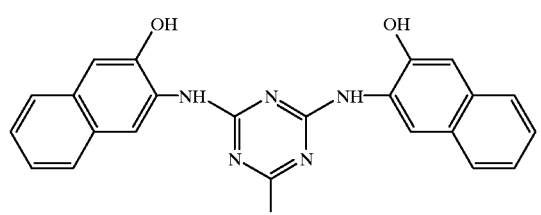

wherein M is as defined above.

There exists a considerable number of activating agents which have found use for the general purpose of attaching ligands to support matrices. These compounds and their method of use are well known to those skilled in the art and, since the nub of the present invention lies in the nature of the ligand attached to the matrix and not in the mode of attachment, any of these activating agents will serve in the preparation of the new matrix-ligand conjugates of the invention. As non-limiting examples of such activating agents there may be mentioned such diverse compounds as cyanogen bromide, cyanuric chloride, epichlorohydrin, divinyl sulphone, p-toluenesulphonyl chloride, 1,1'-carbonyldiimidazole, sodium meta-periodate, 2-fluoro-1-methylpyridiniumtoluene-4-sulphonate, glycidoxypropyltrimethoxysilane and 2,2,2-trifluoroethanesulphonyl chloride. As indicated above, the procedures by which such activating steps are carried out are well known to those skilled in the art.

Similarly, a wide variety of condensing agents may be used to attach the compounds of General Formulae (VI) to support matrices such as agarose, cellulose, dextran, starch, alginate, carrageenan, silica or glass. Again these compounds, and their method of use are well known to those skilled in the art and, again, since the nub of the present invention lies in the nature of the ligand and not in the mode of attachment, any of these condensing agents will serve in the preparation of the new matrix-ligand conjugates of the invention. As non-limiting examples of such condensing agents, there may be mentioned N-ethoxycarbonyl-2-ethoxy-1,2-dihydroquinoline, dicyclohexyl carbodiimide and 1-ethyl-3-(3-dimethylaminopropyl)-carbodiimide.

As examples of linking units of General Formula (VI) which may be used to produce compounds of General Formula (VII) there may be mentioned diamines such as ethylene diamine, N,N'-dimethylethylene diamine, N-ethylethylene diamine, N-(β-hydroxyethyl)-ethylene diamine, propylene diamine, N-methylpropylene diamine, N-(β-hydroxyethyl)-propylene diamine, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, piperazine, 3-hydroxy-1,5-diaminopentane, m- and p-phenylene diamine, m- and p-aminobenzylamine; amino alcohols such as ethanolamine, N-methylethanolamine, N-propylethanolamine, diethanolamine, 3-hydroxypropylamine, 2,3-dihydroxypropylamine, isopropanolamine, 5-aminopentan-1-ol and 6-aminohexan-1-ol; aminophenols such as o-, m- and p-aminophenol, aminocarboxylic acids such as glycine, N-methylglycine, 3- and 4-aminobutyric acid, 3-aminoisobutyric acid, 5-aminovaleric acid, 6-aminocaproic acid, 7-aminoheptanoic acid, m- and p-aminobenzoic acid; aminophosphonic acids such as m-aminobenzenephosphonic acid and p-aminobenzylphosphonic acid; and aminoarylene vinylsulphone precursors such as aniline-3-β-sulphatoethylsulphone and aniline-4-β-sulphatoethylsulphone.

The reaction of halogenoheterocyclic compounds of General Formula (II) with compounds of General Formulae (III), (IV) and (V) or (VI) may be carried out in an organic solvent which is not miscible with water; or in an organic solvent which is miscible with water, or in a mixture of water and a water miscible organic solvent. Examples of suitable organic solvents which are not miscible with water are toluene, xylene or chlorobenzene; Examples of suitable organic solvents which are miscible with water are acetone, methyl ethyl ketone or dioxan. The first reaction of the halogenoheterocyclic compound may be carried out at temperatures between 0° C. and 25° C., ideally between 0° C. and 5° C.; the second reaction may be carried out at temperatures between 20° C. and 50° C., ideally between 30° C. and 45° C. and the third reaction at temperatures between 20° C. and 100° C. During such reactions, the inorganic acid such as hydrochloric acid or hydrofluoric acid which is produced is neutralised by the use of an acid binding agent such as sodium hydroxide, sodium carbonate, sodium bicarbonate, calcium hydroxide or calcium carbonate.

Additionally, compounds of General Formula (VII) may be reacted with a reactive polymerisable monomer to form a polymerisable compound of General Formula (VIII):

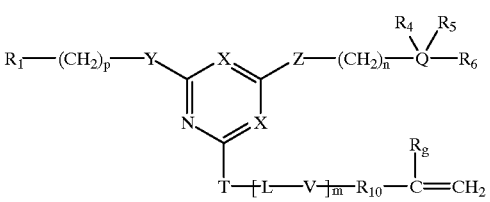

wherein $R_1$, $R_4$, $R_5$, $R_6$, Q, L, T, V, X, Y, Z, m, n and p have the meanings hereinbefore specified; $R_9$ represents a hydrogen atom or an alkyl group containing from 1 to 6 carbon atoms; $R_{10}$ represents a carbonyl group, a methylene group, a —NH—CH$_2$— group or a —S—CH$_2$— group. Examples of reactive polymerisable monomers include acryloyl chloride, methacryloyl chloride, allyl bromide, allylamine or 3,4-epoxybutene. Polymerisable compounds of General Formula (VIII) may be polymerised, optionally in the presence of other polymerisable monomers, to form affinity ligand matrix conjugates of General Formula (I). Such polymerisation procedures are well known to those skilled in the art.

The invention further covers the use of all such affinity ligand-support matrices in the separation, isolation, purification, quantification, identification and characterisation of proteinaceous materials, such as immunoglobulins, insulins, Factor VII, or Human Growth Hormone or analogues, derivatives and fragments thereof and precursors.

Immunoglobulins are a family of proteins, often abbreviated as $I_g$, which share a common structure. Immunoglobulins are also known collectively as antibodies and either word may be used to describe this group of proteins. Immunoglobulins exist in a number of different forms, for example, the most significant antibody types being $I_gA$, $I_gD$, $I_gE$, $I_gG$, $I_gM$ and $I_gY$ and various subclasses thereof. Immunoglobulins may occur in body fluids, such as plasma, ascities, saliva, milk or egg yolk or may be produced using genetic engineering methodologies. Immunoglobulins may be altered by a variety of techniques to confer desirable properties upon them. Such procedures are well known to those skilled in the art and the resulting modified antibodies are also subject to the claims of this invention. As non-limiting Examples of antibody modification techniques, antibody fragments, labelled antibodies, antibody conjugates or antibody-fusion proteins may be obtained through chemical modification, by treatment with one or more enzymes or by a combination of both techniques. There exists a considerable number of chemical modification reagents and enzymes which have found use in antibody modification and these compounds and their use are well known to those skilled in the art. A further way of obtaining modified or novel antibodies is to produce them using genetic engineering methodologies. Such methodologies and their use are well known to those skilled in the art and may be used to produce, for example, antibody fragments or antibody-fusion products. Modified or novel antibodies derived by genetic engineering methodologies are also subject to the claims of this invention.

A valuable group of affinity ligand-support matrices is represented by the General Formula (IX):

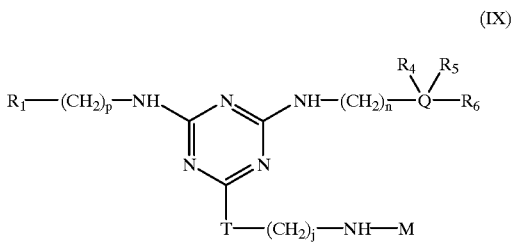

(IX)

wherein $R_1$, $R_4$, $R_5$, $R_6$, M, Q, n and p have the meanings hereinbefore specified and j is an integer between 2 and 20.

An especially valuable group of affinity ligand-support matrices is represented by the general Formula (X):

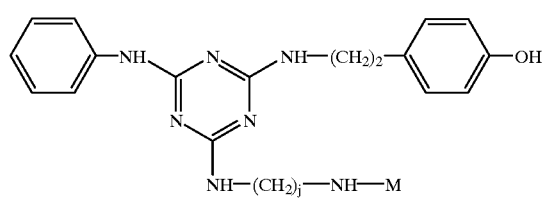

(X)

wherein j and M have the meanings hereinbefore specified.

Typically, reaction of compounds of General Formula (XI)

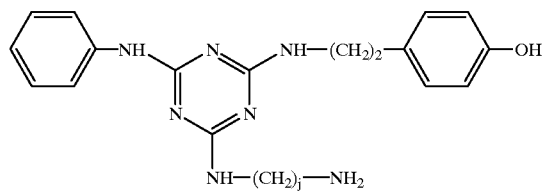

(XI)

with 3-propoxy-(1,2-epoxy)-agarose at temperatures between 10° C. and 30° C. in the presence of an acid binding agent produces novel affinity ligand-matrix conjugates which are of outstanding value in the purification of proteinaceous materials. These new affinity ligand-matrix conjugates possess high affinity for the immunoglobulin group of proteins. This unique property makes them of exceptional value in the separation, isolation, purification quantification, identification and characterisation of proteins of this class.

In another embodiment the invention relates to novel affinity ligands of General (XII)

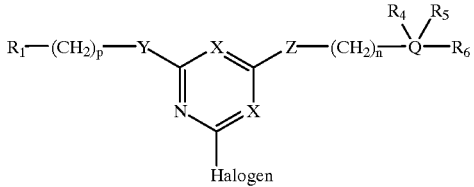

wherein $R_1$, $R_4$, $R_5$, $R_6$, Q, X, Y, Z, n and p have the meanings specified above and Halogen represents a fluorine, chlorine, bromine or iodine atom.

Furthermore, the invention relates to a method of attaching novel affinity ligands of General Formula (XII) as defined above to a matrix of General Formula (V) as defined above by reacting the novel affinity ligands with the matrix at temperatures between –20° C. and 121° C., optionally in the presence of an acid binding agent.

In another embodiment the invention relates to novel affinity ligands of General Formula (XIII):

(XIII)

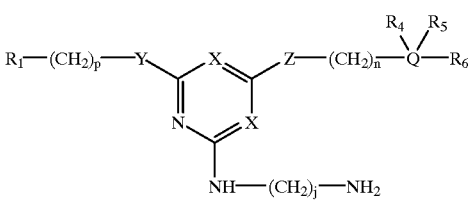

wherein $R_1$, $R_4$, $R_5$, $R_6$, Q, X, Y, Z, m, n and p have the meanings specified above and j is an integer between 2 and 20.

Furthermore the invention relates to a method of preparing above novel affinity ligands of General Formula (XIII) by reacting a compound of above General Formula (XII) with an alkylene diamine of General Formula $H_2N$—$(CH_2)_j$—$NH_2$ at temperatures between 0° C. and 100° C. in the presence of an acid binding agent.

In another embodiment the invention relates to novel affinity ligands of General Formula (XIV):

(XIV)

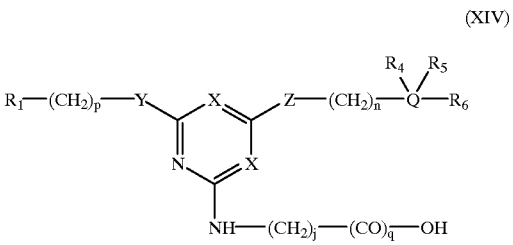

wherein $R_1$, $R_4$, $R_5$, Q, X, Y, Z, m, n and p have the meanings specified above, q is 0 or 1 and j is an integer between 2 and 20.

Furhermore the invention relates to a method of preparing novel affinity ligands of above General Formula (XIV) by reacting a compound of above General Formula (XII) with an amino hydroxy compound of General Formula $H_2N$—$(CH_2)_j$—$(CO)_q$—OH at temperatures between 0° C. and 100° C., optionally in the presence of an acid binding agent.

In another embodiment the invention relates to novel affinity ligands of above General Formula (VIII) wherein $R_1$, $R_4$, $R_5$, $R_6$, L, Q, T, V, X, Y, Z, m, n and p have the meanings specified above; $R_9$ represents a hydrogen atom or an alkyl group containing from 1 to 6 carbon atoms; $R_{10}$ represents a carbonyl group, a methylene group, an —NH—$CH_2$— group or an —S—$CH_2$— group; preferably L is an ethyl, butyl or hexyl group, preferably T represents a —NH— group, preferably V represents a —NH— group and m is prefably 1.

In another embodiment the invention relates to novel affinity ligands of General Formula (XV):

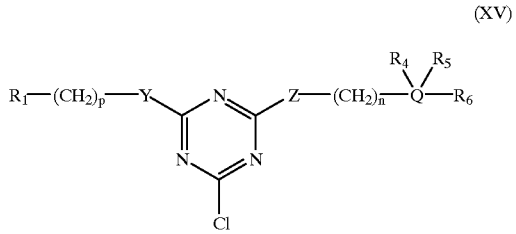

(XV)

wherein R, $R_4$, $R_5$, $R_6$, Q, n and p have the meanings specified above.

In another embodiment the invention relates to novel affinity ligands of General Formula (XVI):

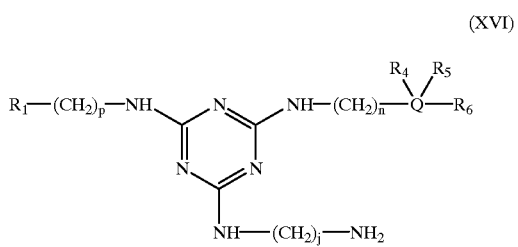

(XVI)

wherein $R_1$, $R_4$, $R_5$, $R_6$, Q, n and p have the meanings specified above and j is an integer between 2 and 20.

In another preferred embodiment the invention relates to affinity ligands of General Formula (XII), (XIII), (XIV), (VIII), (XV) and (XVI) wherein $R_1$ represents a phenyl or naphthyl group each of which is optionally substituted on the benzene or naphthalene ring with one or more independently selected from hydroxyl groups or carboxylic acid groups.

In another preferred embodiment the invention relates to affinity ligands of General Formula (XII), (XIII), (XIV), (VIII), (XV) and (XVI) wherein $R_4$ represents a hydrogen atom, a hydroxyl group, a carboxylic acid group or an amino group.

In another preferred embodiment the invention relates to affinity ligands of General Formula (XII), (XIII), (XIV), (VIII), (XV) and (XVI) wherein $R_5$ represents a hydrogen atom, a hydroxyl group, a carboxylic acid group or an amino group.

In another preferred embodiment the invention relates to affinity ligands of General Formula (XII), (XIII), (XIV), (VIII), (XV) and (XVI) wherein $R_6$ represents a hydrogen atom, a hydroxyl group, a carboxylic acid group or an amino group.

In another preferred embodiment the invention relates to affinity ligands of General Formula (XII), (XIII), (XIV), (VIII), (XV) and (XVI) wherein Q represents a benzene or naphthalene ring.

In another preferred embodiment the invention relates to affinity ligands of General Formula (XII), (XIII), (XIV), and (VIII) wherein X represents a nitrogen atom.

In another preferred embodiment the invention relates to affinity ligands of General Formula (XII), (XIII), (XIV), and (VIII) wherein Y represents a —NH— group.

In another preferred embodiment the invention relates to affinity ligands of General Formula (XII), (XIII), (XIV), and (VIII) wherein Z represents a —NH— group.

In another preferred embodiment the invention relates to affinity ligands of General Formula (XII), (XIII), (XIV), (VIII), (XV) and (XVI) wherein n is 0 or 2.

In another preferred embodiment the invention relates to affinity ligands of General Formula (XII), (XIII), (XIV), (VIII), (XV) and (XVI) wherein p is 0 or 2.

In another preferred embodiment the invention relates to affinity ligands of General Formula (XIII), (XIV) and (XVI) wherein j is 2, 4 or 6.

In another embodiment the invention relates to affinity ligands of above General Formula (XI) wherein j is an integer betweem 2 and 20. Preferred affinity ligands according to the invention are:

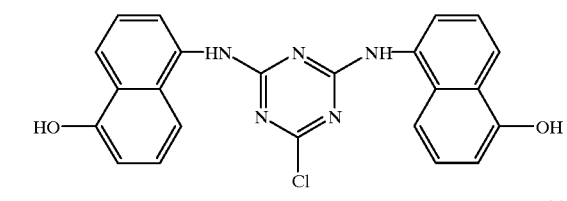

(6)

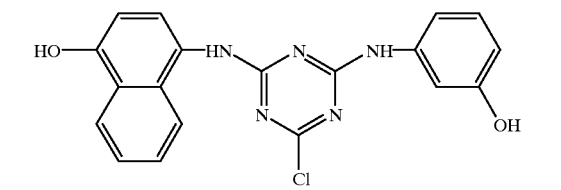

(7)

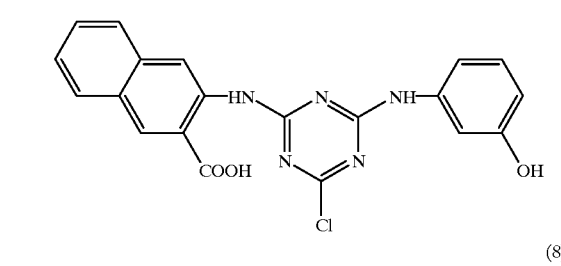

(8)

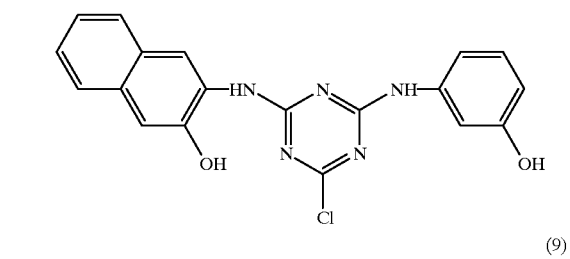

(9)

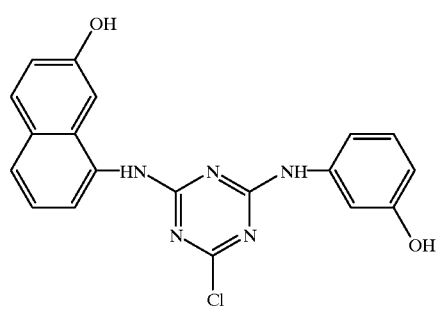

-continued

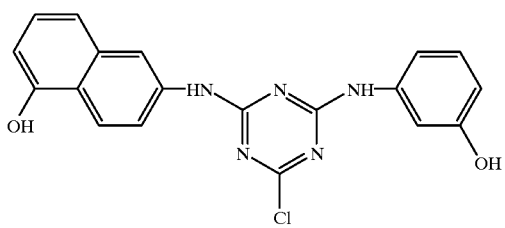
(10)

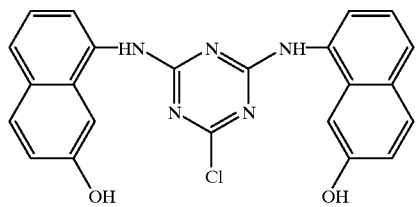
(11)

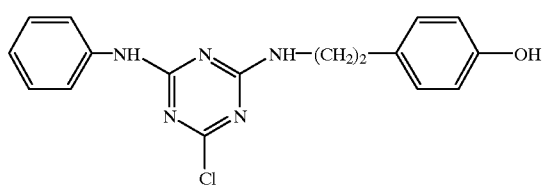
(12)

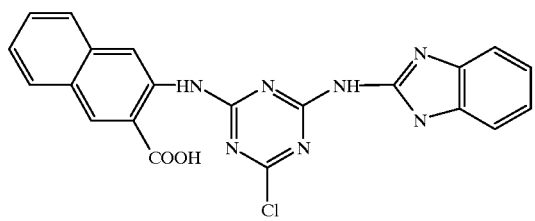
(13)

Furthermore the invention relates to a method of attaching the novel affinity ligands of General Formulae (VII) as defined above, (XIII) as defined above, (XVI) as defined above and (XI) as defined above to carbohydrate or organic polymer matrices by reacting the carbohydrate or organic polymer matrix with an activating agent followed by reaction of the activated matrix with the novel affinity ligand, optionally in the presence of an acid binding agent. The invention also relates to a method of attaching the novel affinity ligands of General Formulae (XIV) as defined above to carbohydrate or organic polymer matrices by condensation with the matrix. The invention furthermore relates to a method of attaching the novel affinity ligands of General Formulae (VII) as defined above, (XIII) as defined above, (XVI) as defined above and (XI) as defined above to metal oxide, glass or silica matrices, optionally coated with an organic polymer by reacting the optionally coated metal oxide, glass or silica matrix with an activating agent followed by reaction of the activated matrix with the novel affinity ligand, optionally in the presence of an acid binding agent. Another embodiment of the invention relates to a method of attaching the novel affinity ligands of General Formulae (XIV) as defined above to metal oxide, glass or silica matrices, optionally coated with an organic polymer by condensation with the matrix. In another embodiment the invention realates to a method of attaching novel affinity ligands of General Formula (XV) as defined above and (XII) as defined in above to a matrix of General Formula (V) as defined above by reacting the novel affinity ligands with the matrix at temperatures between −20° C. and 121° C., optionally in the presence of an acid binding agent. The invention also relates to all the affinity ligand-matrix conjugates, prepared as described in the above methods.

In another embodiment the invention relates to the use of the affinity ligands according to the invention and the affinity ligand-matrix conjugates comprising such ligands according to the invention for the separation, isolation, purification, characterisation, identification or quantification of proteins or proteinaceous materials, such as immunoglobulins or subclasses, fragments, precursors or derivatives thereof, whether derived from natural or recombinant sources e.g. immunoglobulin G (IgG), immunoglobulin M (IgM), immunoglobulin A (IgA) or subclasses, fragments, precursors or derivatives thereof, whether derived from natural or recombinant sources. In another embodiment the invention relates to the separation, isolation, purification, characterisation, identification or quantification of immunoglobulins by any process whereby the said immunoglobulins are applied to affinity ligand-matrix conjugates according to the invention at a pH in the range 5.0 to 12.0 and subsequently removed, eluted or desorbed by reducing the pH to 4.9 or lower.

The invention also relates to a process for the separation or purification of proteinaceous materials comprising carrying out affinity chromatography using as the biospecific ligand a ligand of general formula (a) as defined above.

Another embodiment of the invention relates to the use of the affinity ligands according to the invention and the affinity ligand-matrix conjugates comprising such ligands according to the invention for the separation, isolation, purification, characterisation, identification or quantification of insulins and analogues, derivatives and fragments thereof and precursors, whether derived from natural or recombinant sources and Factor VII, or human Growth Hormone or analogues, derivatives and fragments thereof and precursors.

By way of example, a library comprising more than 60 different ligands were designed. The library was screened with partly purified insulin precursor and selected ligands were immobilised by solid phase synthesis to agarose. The matrices were optimized with respect to coupling technology, length and nature of spacer arm, ligand density etc. resulting in 3 prototypes of dynamic binding capacity of 2–5 mg/ml. A recombinantly derived insulin precursor was purified to more than 95% purity from clarified yeast fermentation broth by a single mimetic affinity purification step under very mild conditions.

An especially preferred use of the affinity ligands according to the invention and the affinity ligand-matrix conjugates comprising such ligands according to the invention is thus the purification of insulins and analogues, derivatives and fragments thereof and precursors, whether derived from natural or recombinant sources. Especially preferred affinity ligand-matrix conjugates for this use comprises a ligand selected among the following:

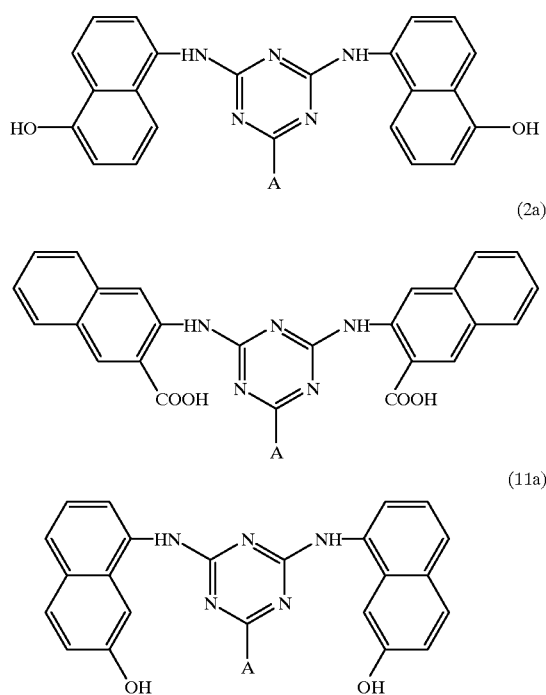

which ligand is attached to a support matrix in position A as specified above, optionally through a spacerarm interposed between the matrix and ligand represented by the general formula (b) as defined above. Preferably, the ligand is 11a, and the support matrix is preferably optionally activated agarose, cellulose, silica or glass.

In another embodiment the invention relates to the separation, isolation, purification, characterisation, identification or quantification of insulins or insulin analogues or derivatives thereof and precursors by any process whereby the said insulins, insulin derivatives, analogues, and precursors are applied to affinity ligand-matrix conjugates according to the invention at a pH in the range 4,0 to 9,0 and subsequently removed, eluted or desorbed by reducing the pH to 3,99 or lower or to 9,01 or higher. The elution procedure can e.g. alternatively be carried out by lowering the ionic strength or by addition of co-solvents such as organic solvents.

The invention will now be described in further detail with reference to the following examples. The examples are provided for illustrative purposes, and are not to be construed as limiting the scope of the invention in any way.

EXAMPLE 1

This Example illustrates the synthesis of a typical affinity ligand defined by the reaction of halogenoheterocyclic compounds of General Formula (II) with compounds of General Formula (III) and (IV).

19.8 parts of aniline were dissolved in 50 parts of acetone and the solution run into a suspension formed by pouring a solution of 36.8 parts of cyanuric chloride in parts of 200 parts of acetone into a mixture of 50 parts of ice and 50 parts of water. The mixture was stirred for 2 hours during which time the pH was maintained at between 6 and 7 by the addition of a solution of 16.8 parts of sodium hydrogen carbonate in 300 parts of water. At the end of this time, the precipitate of 2-anilino-4,6-dichloro-1,3,5-triazine was filtered off, washed with water, dried in vauco and crystallised from dichloromethane.

A solution of 2.74 parts of tyramine in a mixture of 50 parts of acetone and 10 parts of water was added to a solution of 4.82 parts of 2-anilino-4,6-dichloro-1,3,5-triazine in 100 parts of acetone. The mixture was heated at 50° C. and held at this temperature for 2 hours whilst the pH was maintained between 6 and 7 by the addition of a solution of 1.68 parts of sodium hydrogen carbonate in 30 parts of water. At the end of this time the precipitate of 2-anilino-4-[β-(4'-hydroxyphenyl)-ethylamino]-6-chloro-1,3,5-triazine was filtered off, washed with water and dried in vacuo.

EXAMPLE 2

This Example illustrates the immobilisation of the product of Example 1 onto a solid phase support.

Ten parts of agarose bearing amino groups was transferred into an acetone solvent by solvent exchange using 100 parts of 30% aqueous acetone followed by 100 parts of 70% aqueous acetone and then 100 parts of acetone. One part of 2-anilino-4-[-β-(4'-hydroxyphenyl)-ethylamino]-6-chloro-1,3,5-triazine was dissolved in 20 parts of acetone and warmed to 50° C. This warm acetone solution was added to the acetone suspension of an agarose derivative bearing amino groups. A solution of 0.42 parts of sodium hydrogen carbonate in 5 parts of water was added to the resultant suspension and the mixture then stirred for 16 hours at 50° C. At the end of this time, the agarose support matrix was washed free of non-bonded 2-anilino-4-[-β-(4'-hydroxyphenyl)-ethylamino]-6-chloro-1,3,5-triazine with acetone. The resulting derivatised affinity support was then transferred back to water by washing first with 70% aqueous acetone, then with 30% aqueous acetone and finally with water.

EXAMPLE 3

This Example demonstrates the use of the novel affinity matrix described in Example 2 as a specific chromatography matrix for immunoglobulins.

One and one quarter parts of human plasma was diluted with 3.75 parts of aqueous phosphate buffer having a pH of 7 and a concentration of 10 millimoles per liter and applied to a column consisting of 1 part of affinity matrix whose preparation is described in Example 2. The affinity column was then washed with phosphate buffer until UV monitoring of the wash liquors showed that all non-bound protein had been removed. The affinity matrix was then washed with a citrate buffer having a pH of 3.8 and a concentration of 0.2 millimoles per liter until UV monitoring of the wash liquor showed that removal of bound protein had ceased. The protein contained in this wash liquor was shown to be immunoglobulin G.

Table 1 gives further Examples of novel affinity ligands of the invention which may be prepared by the method of Example 1 but replacing the 36.8 parts of cyanuric chloride used in Example 1 by the corresponding amount of the halogenoheterocyclic compound listed in Column II of the Table; replacing the 19.8 parts of aniline used in Example 1 by the corresponding amount of the amine listed in Column III of the Table and replacing the 2.74 parts of tyramine used in Example 1 by the corresponding amount of the amine listed in Column IV of the Table. The number of the Example is given in Column I of the Table.

TABLE 1

| I | II | III | IV |
|---|---|---|---|
| 4 | 5-cyano-2,4,6-trichloropyrimidine | aniline | tyramine |
| 5 | 5-chloro-2,4,6-trifluoropyrimidine | aniline | tyramine |
| 6 | cyanuric chloride | tyramine | tyramine |
| 7 | cyanuric chloride | aniline | 4-hydroxy-benzyl-amine |
| 8 | cyanuric chloride | aniline | benzylamine |
| 9 | cyanuric chloride | N-methyl-aniline | 4-hydroxy-benzyl-amine |
| 10 | cyanuric chloride | p-anisidine | p-aminophenol |
| 11 | cyanuric chloride | aniline | 4-acetylamino-benzylamine |
| 12 | cyanuric chloride | p-toluidine | tyramine |
| 13 | cyanuric chloride | p-chloro-aniline | tyramine |
| 14 | cyanuric chloride | p-aminophenol | tyramine |
| 15 | cyanuric chloride | cyclohexyl-amine | tyramine |
| 16 | cyanuric chloride | β-phenyl-ethylamine | tyramine |
| 17 | cyanuric chloride | 4-hydroxy-benzylamine | tyramine |
| 18 | cyanuric chloride | 4-hydroxy-benzylamine | 4-hydroxy-benzyl-amine |
| 19 | cyanuric chloride | benzylamine | tyramine |
| 20 | cyanuric chloride | tyramine | 3-methylsulphonyl-aniline |
| 21 | cyanuric chloride | N-tert-butyl-benzylamine | tyramine |
| 22 | cyanuric chloride | N-isopropyl-benzylamine | tyramine |
| 23 | cyanuric chloride | p-amino-acetanilide | tyramine |
| 24 | cyanuric chloride | di-isopropyl-amine | tyramine |
| 25 | cyanuric chloride | aniline | N-benzyltyramine |
| 26 | cyanuric chloride | tyramine | N-benzyltyramine |
| 27 | cyanuric chloride | p-amino-benzamide | tyramine |
| 28 | cyanuric chloride | p-aminobenzene sulphonamide | tyramine |
| 29 | cyanuric chloride | p-amino-benzoic acid | tyramine |
| 30 | cyanuric chloride | p-amino-benzoic acid | 1-amino-4-naphthol |
| 31 | cyanuric chloride | p-aminophenol | 1-amino-5-naphthol |
| 32 | cyanuric chloride | p-amino-benzoic acid | 1-amino-5-naphthol |
| 33 | cyanuric chloride | p-aminophenol | p-aminophenol |
| 34 | cyanuric chloride | m-amino-benzoic acid | aniline |
| 35 | cyanuric chloride | m-amino-benzoic acid | tyramine |
| 36 | cyanuric chloride | 1-amino-5-naphthol | 1-amino-5-naphthol |
| 37 | cyanuric chloride | m-aminophenol | 1-amino-5-naphthol |
| 38 | cyanuric chloride | 1-amino-4-naphthol | 1-amino-5-naphthol |

These ligands described in Examples 4–38 may be attached to an agarose matrix by the procedure detailed in Example 2 and used in the purification of immunoglobulin G by the procedure given in Example 3.

EXAMPLE 39

6 Parts of ethylene diamine were added to a solution of 2.5 parts of 2-anilino-4-[β-(4'-hydroxyphenyl)-ethylamino]-6-chloro-1,3,5-triazine in 20 parts of toluene and the mixture heated at 100° C. for 16 hours. The toluene was then evaporated off from the mixture under reduced pressure and the residue washed 5 times with 100 parts of water and then dried at 70° C.

Table 2 gives further Examples of novel affinity ligands of the invention which may be prepared by the method of Example 39 but replacing the 2.5 parts of 2-anilino-4-[β-(4'hydroxyphenyl)-ethylamino]-6-chloro-1,3,5-triazine used in Example 39 by the corresponding amount of the chlorotriazine listed in Column II of Table 2 and replacing the ethylene diamine used in Example 39 by the corresponding amount of the diamine or amino hydroxy compound listed in Column III of Table 2.

TABLE 2

| I | II | III |
|---|---|---|
| 40 | Chlorotriazine described in Example 1 | propylene diamine |
| 41 | Chlorotriazine described in Example 1 | 1,6-diaminohexane |
| 42 | Chlorotriazine described in Example 1 | 1,8-diaminooctane |
| 43 | Chlorotriazine described in Example 1 | 1,9-diaminononane |
| 44 | Chlorotriazine described in Example 1 | 1,10-diaminodecane |
| 45 | Chlorotriazine described in Example 1 | 1,12-diaminododecane |
| 46 | Chlorotriazine described in Example 14 | 1,6-diaminohexane |
| 47 | Chlorotriazine described in Example 30 | 1,6-diaminohexane |
| 48 | Chlorotriazine described in Example 31 | 1,6-diaminohexane |
| 49 | Chlorotriazine described in Example 33 | 1,6-diaminohexane |
| 50 | Chlorotriazine described in Example 35 | 1,6-diaminohexane |
| 51 | Chlorotriazine described in Exampie 38 | 1,6-diaminohexane |
| 52 | Chlorotriazine described in Example 1 | N,N'-dimethylethylene diamine |
| 53 | Chlorotriazine described in Example 1 | N-β-hydroxyethylethylene diamine |
| 54 | Chlorotriazine described in Example 1 | piperazine |
| 55 | Chlorptriazine described in Example 1 | ethanolamine |
| 56 | Chlorotriazine described in Example 1 | diethanolamine |
| 57 | Chlorotriazine described in Example 1 | isopropanolamine |

EXAMPLE 58

This Example illustrates the immobilisation of the compound produced in Example 39 onto a solid phase support.

Sixty parts of agarose bearing epoxide groups was washed with 300 parts of water followed by 300 parts of a solution consisting of 5.95 parts of potassium hydrogen carbonate dissolved in 180 parts of methanol and 120 parts of water. One part of the compound prepared according to Example 39 was dissolved in 60 parts of methanol and added to a solution of 40 parts of aqueous potassium hydrogen carbonate solution. One hundred parts of this aqueous methanol solution was then added to the prepared suspension of 60 parts of agarose bearing epoxy groups and the resulting suspension gently agitated at ambient room temperature for 16 hours. The agarose based matrix obtained was washed first with a mixture of 360 parts of methanol and 240 parts of water, and then with 600 parts of water.

EXAMPLE 59

If Example 3 is repeated but replacing the column consisting of 1 part of affinity matrix whose preparation is described in Example 2 by a column consisting of 1 part of affinity matrix whose preparation is described in Example 58. The protein contained in the pH 3.8 wash liquor was again shown to be immunoglobulin G.

EXAMPLE 60

This Example illustrates the immobilisation of the product obtained in Example 39 onto a solid phase support.

Eighty parts of agarose was washed with 1050 parts of water followed by 1050 parts of 30% aqueous acetone, then 1050 parts of 70% aqueous acetone and finally 1425 parts of acetone. The eighty parts of agarose were then suspended in 100 parts of acetone and the suspension warmed to 37° C. Fifteen parts of p-toluenesulphonyl chloride dissolved in 15 parts of pyridine and 25 parts of acetone was added to the agarose suspension and the mixture kept at 37° C. for 8 hours. The activated agarose was then washed with 225 parts of acetone followed by 225 parts of 70% aqueous acetone, then 225 parts of 30% aqueous acetone and, finally, 225 parts of water.

Fortyfive parts of this activated matrix was washed with 225 parts of a solution consisting of 2.3 parts of potassium hydrogen carbonate dissolved in a mixture of 178 parts of methanol and 47 parts of water. A solution of 0.75 parts of the compound prepared according to Example 39 in a mixture of 45 parts of methanol and 30 parts of water containing 1.5 parts of potassium hydrogen carbonate was added to the activated agarose suspension and the mixture then left to stand for 16 hours at room temperature. The resulting affinity matrix was washed with 270 parts of methanol and 180 parts of water containing 9 parts of potassium hydrogen carbonate, followed by 450 parts of water.

Prior to use, 115 parts of the resulting affinity matrix was suspended in a solution of 0.36 parts of sodium hydroxide in 45 parts of water.

EXAMPLE 61

If Example 3 is repeated but replacing the column consisting of 1 part of the affinity matrix whose preparation is described in Example 2 by a column consisting of 1 part of the affinity matrix whose preparation is described in Example 60, the protein contained in the pH 3.8 wash liquor was again shown to be immunoglobulin G.

EXAMPLE 62

Ten parts of the affinity matrix prepared according to Example 60 was allowed to stand in a phosphate buffer having a pH of 8.0 for 16 hours. Example 3 was repeated but replacing the matrix used therein with an equivalent amount of this new affinity matrix and using cell free supernatant from murine immunoglobulin cell culture medium in place of the human plasma used in Example 3. The protein contained in the pH 3.8 wash liquor was again shown to be murine immunoglobulin M.

Table 3 gives further Examples of the attachment of the novel affinity ligands of the invention which may be prepared by the method of Example 58 but replacing the novel affinity ligand used in Example 58 by the corresponding amount of the novel affinity ligand specified in Column II of Table 3 and by replacing the 39 parts of epichlorohydrin activated agarose used in Example 58 by the corresponding amount of the carbohydrate listed in Column III of Table 3 activated by the reagent listed in Column IV of Table 3.

TABLE 3

| I | II | III | IV |
|---|---|---|---|
| 61 | Ligand of Example 39 | agarose | 1,4-butanediol diglycidyl ether |
| 62 | Ligand of Example 39 | agarose | cyanogen bromide |
| 63 | Ligand of Example 39 | agarose | epichlorohydrin |
| 64 | Ligand of Example 39 | agarose | sodium metaperiodate |
| 65 | Ligand of Example 39 | agarose | 2,2,2-trifluoro--ethanesulphonyl-chloride |
| 66 | Ligand of Example 39 | agarose | 1,1'-carbonyldi--imidazole |
| 67 | Ligand of Example 39 | agarose | 2-fluoro-1-methyl--pyridinium toluene-4-sulphonate |
| 68 | Ligand of Example 39 | agarose | divinyl sulphone |
| 69 | Ligand of Example 39 | agarose | cyanuric chloride |

EXAMPLE 70

If the preparation of the ligand detailed in Example 1 is repeated but reacting the 2.74 parts of tyramine with 4.84 parts of 2-phenoxy-4,6-dichloro-1,3,5-triazine instead of 4.82 parts of 2-anilino-4,6-dichloro-1,3,5-triazine, there is obtained 2-phenoxy-4-[β-(4'-hydroxyphenyl)-ethylamino]-6-chloro-1,3,5-triazine, which may be used in place of 2-anilino-4-[β-(4'-hydroxyphenyl)-ethylamino]-6-chloro-1,3,5-triazine in the preparation of an affinity matrix by the method of Example 2. Again, immunoglobulin G may be conveniently isolated from human plasma by the technique described in Example 3.

EXAMPLE 71

Use of 5.16 parts of 2-phenylthio-4,6-dichloro-1,3,5-triazine in place of the 4.84 parts of 2-phenoxy-4,6-dichloro-1,3,5-triazine used in Example 70 gives 2-phenylthio-4-[β-(4'-hydroxyphenyl)-ethylamino]-6-chloro-1,3,5-triazine, which may be similarly used to purify immunoglobulin G.

EXAMPLE 72

This Example illustrates an alternative approach to producing affinity ligand-matrix conjugates as exemplified in Example 2 and Example 58.

Ten parts of agarose bearing aminoethylamino groups were stirred at 0–5° C. with 5 parts of acetone and 5 parts of an aqueous phosphate buffer having a pH of 7 and a concentration of 0.5 moles per liter. To this suspension was added 2.5 parts of a solution comprising 1 part of cyanuric chloride in 10 parts of acetone and the mixture then agitated for an hour at a temperature of 0–5° C. The resulting dichlorotriazine activated agarose was washed sequentially with 50 parts of 50% aqueous acetone, 50 parts of water, 50 parts of 50% aqueous acetone and 100 parts of water. Twenty parts of the washed dichlorotriazine activated agarose was added to 20 parts of an aqueous solution comprising 1 part of tyramine in 200 parts of water and the resulting suspension agitated for 16 hours at ambient room temperature. At the end of this period, the resulting derivatised matrix was washed with 200 parts of water and added to 20 parts of an aqueous solution comprising 0.55 parts of aniline dissolved in 200 parts of water. The resulting suspension was agitated for 16 hours at 90° C. after which time the derivatised matrix was washed with 200 parts of water.

EXAMPLE 73

If Example 3 is repeated but replacing the column consisting of 1 part of the affinity matrix whose preparation is described in Example 2 by a column consisting of 1 part of the affinity matrix whose preparation is described in Example 72, the protein contained in the pH 3.8 wash liquor was again shown to be immunoglobulin G.

EXAMPLE 74

This example illustrates the synthesis of a library of affinity ligand-matrix conjugates of this invention which may be subsequently screened to determine their protein binding properties.

One part of agarose bearing amino groups was mixed with 1 part 1 M potassium phosphate buffer, pH 7.0 and settled under gravity. The buffered amine agarose was transferred to a reaction vessel and mixed at 0–5° C. with 0.5 parts 0.5M potassium phosphate buffer, pH 7.0 and 0.5 parts acetone. One quarter of a part of a solution comprising 1 part cyanuric chloride in 10 parts acetone was added and the mixture stirred at 0–5° C. for 1 hour, after which the mixture was filtered and washed sequentially with 10 parts 50% acetone, 6 parts water, 6 parts 50% acetone and 10 parts water to provide 2,4-dichloro-s-triazin-6-yl activated agarose.

One part of the 2,4-dichloro-s-triazin-6-yl activated agarose was added to 5 mole equivalents of the amine compound listed in Column II of Table 4 dissolved in 2 to 3 parts of a solution comprising 1 part acetone and 1 part water and adjusted to neutral pH by addidtion of sodium hydroxide. The suspension was mixed for 24 hours at 30° C. The resulting monochloro-s-triazin-6-yl activated agaroses were washed sequentially with 10 parts of dimethylformamide, 10 parts of a solution comprising 3 parts propan-2-ol and 7 parts 0.2M sodium hydroxide, 10 parts of water and settled under gravity.

One part of the monochloro-s-triazin-6-yl-activated agarose was added to 5 mole equivalents of the amine compound listed in Column III of Table 4 dissolved in 2 to 3 parts of a solution comprising 1 part dimethylformamide and 1 part water and adjusted to neutral pH by addition of sodium hydroxide. The suspension was mixed for 72 hours at 85 to 95° C. The resulting affinity ligand-matrix conjugates were washed sequentially with 10 parts of dimethylformamide, 10 parts of a solution comprising 3 parts propan-2-ol and 7 parts 0.2M sodium hydroxide, 10 parts of water and settled under gravity. A library of affinity ligand-matrix conjugates of this Invention was synthesised, Examples of which are identified in Column I of Table 4.

TABLE 4

| I | II | III |
|---|---|---|
| 75 | 1,3-diaminopropane | tyramine |
| 76 | 1,3-diaminopropane | N-benzylphenethylamine |
| 77 | 1,4-diaminobutane | 3-aminophenol |
| 78 | 1,4-diaminobutane | tyramine |
| 79 | 1,4-diaminobutane | 1-amino-5-naphthol |
| 80 | 1,4-diaminobutane | N-isopropylbenzylamine |
| 81 | 1,4-diaminobutane | N-benzylphenethylamine |
| 82 | aniline | diaminopropane |
| 83 | aniline | aniline |
| 84 | aniline | 3-aminophenol |
| 85 | aniline | 3-aminobenzoic acid |
| 86 | aniline | tyramine |
| 87 | aniline | 1-amino-4-naphthol |
| 88 | aniline | 1-amino-2-naphthol |
| 89 | aniline | 3-amino-2-naphthol |
| 90 | aniline | 1-amino-6-naphthol |
| 91 | aniline | N-isopropylbenzylamine-4-phenylbutylamine |
| 92 | aniline | N-benzylphenethylamine |
| 93 | 3-aminophenol | 3-aminophenol |
| 94 | 3-aminophenol | 1-amino-5-naphthol |
| 95 | 1,6-diaminohexane | tyramine |
| 96 | 1,6-diaminohexane | 4-phenylbutylamine |
| 97 | 3-aminobenzoic acid | 1-amino-5-naphthol |
| 98 | tyramine | tyramine |
| 99 | tyramine | 1-amino-5-naphthol |
| 100 | tyramine | 1-amino-7-naphthol |
| 101 | tyramine | 1-amino-6-naphthol |
| 102 | 1-amino-5-naphthol | aniline |
| 103 | 1-amino-5-naphthol | 3-aminophenol |
| 104 | 1-amino-5-naphthol | 4-aminobenzoic acid |
| 105 | 1-amino-5-naphthol | 3,5-diaminobenzoic acid |
| 106 | 1-amino-5-naphthol | benzylamine |
| 107 | 1-amino-5-naphthol | tyramine |
| 108 | 1-amino-5-naphthol | 1-amino-5-naphthol |
| 109 | 1-amino-7-naphthol | 3-aminophenol |
| 110 | 1-amino-7-naphthol | 1-amino-7-naphthol |
| 111 | 1-amino-4-naphthol | 3-aminophenol |
| 112 | 1-amino-4-naphthol | 1-amino-4-naphthol |
| 113 | 1-amino-2-naphthol | 3-aminophenol |
| 114 | 1-amino-2-naphthol | 1-amino-2-naphthol |
| 115 | 3-amino-2-naphthol | 3-aminophenol |
| 116 | 3-amino-2-naphthol | 3-amino-2-naphthol |
| 117 | 1-amino-6-naphthol | 3-aminophenol |
| 118 | 1-amino-6-naphthol | 1-amino-6-naphthol |
| 119 | 2-amino-1-naphthol | 3-aminophenol |
| 120 | 2-amino-1-naphthol | 2-amino-1-naphthol |
| 121 | 6-amino-1-naphthol | 3-aminophenol |
| 122 | 6-amino-1-naphthol | 6-amino-1-naphthol |
| 123 | 1-amino-6-naphthalenesulphonic acid | 3,5-diaminobenzoic acid |
| 124 | 1-amino-6-naphthalenesulphonic acid | benzylamine |
| 125 | 1-amino-6-naphthalenesulphonic acid | tyramine |
| 126 | 3-amino-2-napthoic acid | 3-aminophenol |
| 127 | 3-amino-2-napthoic acid | 3-amino-2-napthoic acid |

EXAMPLE 128

This example demonstrates the screening process by which the protein binding properties of affinity ligand-matrix conjugates described in example 74 may be identified.

Chromatography columns of 1 ml total volume were packed with affinity ligand-matrix conjugates of Examples 75–127. The columns were equilibrated by flushing with 10 ml of 50 mM sodium phosphate buffer, pH 8.0. One ml of a solution comprising 1.5 mg of human IgG per ml of 50 mM sodium phosphate buffer, pH 8.0 was applied to each chromatography column which were subsequently washed with 10 ml of 50 mM sodium phosphate buffer, pH 8.0 to remove non-bound IgG. Bound IgG was eluted by flushing each column with 5 ml of 50 mM sodium citrate buffer, pH 3.0. The IgG content of the wash and elution fractions was determined by measurement of absorbance at 280 nm against a buffer blank. Analysis of the results revealed affinity ligand-matrix conjugates of Examples 75 to 127 all exhibited human IgG binding. Of these, almost quantitative elution of bound IgG was achieved for affinity ligand-matrix conjugates of Examples 92, 99, 101, 102, 103, 111, 113 and 119 which, as a consequence, are considered to be of exceptional value in the separation, isolation or purification of human IgG.

EXAMPLE 129

Selective binding and elution of Recombinant Coagulation Factor VIIa (rFVIIa) applied to the affinity matrix according to Example 181 from cell culture media.

Procedure:

0.85 ml settled volume of the affinity matrix prepared as in example 181 was packed into a 5 by 50 mm column (Pharmacia HR 5/5) and equilibrated with 20 mL of buffer A: 20 mM Tris, 50 mM NaCl, 5 mM $CaCl_2$, pH 8.0. 5 ml of conditioned BHK Cell culture supernatant enriched with 1.4 mg rFVIIa was applied to the packed column.

After washing off non-binding proteins with 10 mL of buffer A, rFVIIa was eluted by applying 5 mL of buffer B: 20 mM Tri-Sodium-Citrate, 50 mM Tris pH 8.0.

The flow rate during the chromatographic procedure was 0.3 mL/minute.

The column effluent was passed through an in line UV-monitor and collected in 1 mL fraction, and each fraction analyzed for the content of rFVIIa and total protein by analytical reversed phase High Performance Liquid Chromatography(RP-HPLC)

Results:

The UV- monitor out put showed that most of the UV (280 nm) absorbing material came out during applying the supernatant and the following wash with buffer A. During the following elution with buffer B a distinct peak was monitored, that matched the expected size for the applied amount of rFVIIa.

The RP-HPLC analysis of the collected fractions showed that 90% of the applied amount of rFVIIa came out in the fractions during elution with buffer B. The purity of rFVIIa in these fractions were above 95%.

The results show that selective binding of rFVIIa from enriched culture media to the used ligand is achieved.

EXAMPLE 130

Purification of insulin B-chain$^{1-29}$-A-A-K-insulin A-chain$^{1-21}$ on an affinity ligand-matrix conjugate according to Example 171:

255 mg of insulin B-chain$^{1-29}$-Ala-Ala-Lys-insulin A-chain$^{1-21}$, (batch A202558) was suspended in 51 ml of $H_2O$. 10 drops of 1 M acetic acid were added to solubilize the precursor. 0.2 M potassium citrate pH 5.5 was added to a total volume of 510 ml resulting in a solution of 0.12 mg/ml (by RP-HPLC analysis). pH was measured to 5.53, the ionic strength to 30.0 mS/cm and the redox potential to 273 mV.

400 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 12 fractions of 5.0 ml were collected.

The column was cleaned with 50 ml of 0.5 M NaOH and regenerated with 50 ml of 0.1 M citric acid, 60% v/v ethanol.

Samples for RP-HPLC analysis were diluted with 2 M acetic acid prior to analysis.

| Sample | Identification | M13 conc. | Volume | Amount | % |
|---|---|---|---|---|---|
| Application | E091b | 0.12 mg/ml | 400 ml | 48.8 mg | 100 |
| Run through | E091c | 0.00 mg/ml | | 0.0 mg | 0 |
| Wash | E093a | 0.00 mg/ml | | 0.0 mg | 0 |
| Fraction 3 | E093b | 0.01 mg/ml | 5.0 ml | 0.1 mg | |
| Fraction 4 | E093c | 5.00 mg/ml | 5.0 ml | 25.0 mg | |
| Fraction 5 | E093d | 2.62 mg/ml | 5.0 ml | 13.1 mg | |
| Fraction 6 | E093e | 0.52 mg/ml | 5.0 ml | 2.6 mg | |
| Fractions | | | | 40.8 mg | 83 |

Thus a total recovery of 83% was obtained.

The purity of the product was determined to 94% by RP-HPCL analysis. The remaining impurities were insulin related.

EXAMPLE 131

Purification of des-Thr$^{B30}$-insulin on an affinity ligand-matrix conjugate according to Example 171:

150 mg of des-Thr$^{B30}$-insulin (INS-J-009) precipitate was suspended in 50 ml $H_2O$. 5 drops of 2 M acetic acid were added to dissolve the suspension. 0.2 M of potassium citrate pH 5.5 was added to a volume of 500 ml resulting in a concentration of 0.076 mg/ml (by RP-HPLC analysis). pH was measured to 5.52, the ionic strength to 30.0 mS/cm and the redox potential to 264 mV. 400 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 10 fractions of 5.0 ml were collected.

The column was cleaned with 50 ml of 0.5 M NaOH and regenerated with 50 ml of 0.1 M citric acid, 60% v/v ethanol.

Samples for RP-HPLC analysis were diluted with 2 M acetic acid prior to analysis.

| Sample | Identification | M13 conc. | Volume | Amount | % |
|---|---|---|---|---|---|
| Application | E105a | 0.076 mg/ml | 400 ml | 30.0 mg | 100 |
| Run through | E105b | 0.00 mg/ml | | 0.0 mg | 0 |
| Wash | E105d | 0.00 mg/ml | | 0.0 mg | 0 |
| Fraction 3 | E105e | 0.00 mg/ml | 5.0 ml | 0.0 mg | 0 |
| Fraction 4 | E105f | 0.41 mg/ml | 5.0 ml | 2.1 mg | |
| Fraction 5 | E105n | 1.93 mg/ml | 5.0 ml | 9.7 mg | |
| Fraction 6 | E105o | 1.14 mg/ml | 5.0 ml | 5.7 mg | |
| Fraction 7 | E105p | 0.48 mg/ml | 5.0 ml | 2.4 mg | |
| Fraction 8 | E105j | 0.31 mg/ml | 5.0 ml | 1.6 mg | |
| Fractions | | | | 21.5 mg | 71% |

Thus a total recovery of 71% was obtained.

The purity of the product was determined to 91% by RP-HPCL analysis. the remaining impurities were insulin related.

EXAMPLE 132

Purification of insulin B-chain$^{1-29}$-A-A-K-insulin A-chain$^{1-21}$ on an affinity ligand-matrix conjugate according to Example 145:

2 l of centrifuged broth (batch 628) was adjusted to pH 5.5 with 5 M NaOH and filtered through a Leitz Tiefenfilter (Seitz EK) filter followed by filtration through a Leitz Tiefenfilter (Seitz EKS) filter. The concentration was measured to 0.006 mg/ml by RP-HPLC. The ionic strength was measured to 12.2 mS/cm and the redox potential to 316 mV.

1000 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 11 fractions of 5.0 ml were collected.

The column was cleaned with 50 ml of 0.5 M NaOH and regenerated with 50 ml of 0.1 M citric acid, 60% v/v ethanol.

Samples for RP-HPLC analysis were diluted with 2 M acetic acid prior to analysis.

| Sample | Identification | M13 conc. | Volume | Amount | % |
|---|---|---|---|---|---|
| Application | E111e | 0.006 mg/ml | 1000 ml | 6.0 mg | 100 |
| Run through | E115a | 0.00 mg/ml | | 0.0 mg | 0 |
| Wash | E115b | 0.00 mg/ml | | 0.0 mg | 0 |
| Fraction 3 | E115c | 0.00 mg/ml | 5.0 ml | 0.0 mg | 0 |

-continued

| Sample | Identification | M13 conc. | Volume | Amount | % |
|---|---|---|---|---|---|
| Fraction 4 | E115d | 0.58 mg/ml | 5.0 ml | 2.9 mg | |
| Fraction 5 | E115e | 0.11 mg/ml | 5.0 ml | 0.6 mg | |
| Fraction 6 | E115f | 0.04 mg/ml | 5.0 ml | 0.2 mg | |
| Fraction 7 | E115g | 0.02 mg/ml | 5.0 ml | 0.1 mg | |
| Fractions | | | | 3.8 mg | 63% |

Thus a total recovery of 63% was obtained.
The purity of the product was determined to 88% by RP-HPLC analysis. The remaining impurities were insulin related.

EXAMPLE 133

Purification of insulin B-chain$^{1-29}$A-A-K-insulin A-chain-$^{1-21}$ on an affinity ligand-matrix conjugate according to Example 171:

2 l of centrifuged broth (batch 628) was adjusted to pH 5.5 with 5 M NaOH and filtered through a Leitz Tiefenfilter (Seitz EK) filter followed by filtration through a Leitz Tiefenfilter (Seitz EKS) filter. The concentration was measured to 0.006 mg/ml by RP-HPLC. The ionic strength was measured to 12.2 mS/cm and the redox potential to 316 mV.

1000 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 11 fractions of 5.0 ml were collected.

The column was cleaned with 50 ml of 0.5 M NaOH and regenerated with 50 ml of 0.1 M citric acid, 60% v/v ethanol. Samples for RP-HPLC analysis were diluted with 2 M acetic acid prior to analysis.

| Sample | Identification | M13 conc. | Volume | Amount | % |
|---|---|---|---|---|---|
| Application | E111e | 0.006 mg/ml | 830 ml | 5.0 mg | 100 |
| Run through | E113a | 0.00 mg/ml | | 0.0 mg | 0 |
| Wash | E113b | 0.00 mg/ml | | 0.0 mg | 0 |
| Fraction 3 | E113c | 0.00 mg/ml | 5.0 ml | 0.0 mg | 0 |
| Fraction 4 | E113d | 0.58 mg/ml | 5.0 ml | 2.9 mg | |
| Fraction 5 | E113e | 0.10 mg/ml | 5.0 ml | 0.5 mg | |
| Fraction 6 | E113f | 0.04 mg/ml | 5.0 ml | 0.2 mg | |
| Fraction 7 | E113g | 0.02 mg/ml | 5.0 ml | 0.1 mg | |
| Fractions | | | | 3.7 mg | 74% |

Thus a total recovery of 74% was obtained.
The purity of the product was determined to 86% by RP-HPLC analysis. The remaining impurities were insulin related.

EXAMPLE 134

Purification of EEAEPK-insulin B-chain(1-29)-AAK-insulin A-chain(1-21) on an affinity ligand-matrix conjugate according to Example 171:

Centrifuged yeast broth (batch Y44) was filtered through a Leitz Tiefenfilter (Seitz EK) filter resulting in a concentration of 0.35 mg/ml (by RP-HPLC analysis). pH was measured to 5.27, the ionic strength to 7.38 mS/cm and the redox potential to 221 mV.

120 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 11 fractions of 5.0 ml were collected.

The column was cleaned with 50 ml of 0.5 M NaOH and regenerated with 50 ml of 0.1 M citric acid, 60% v/v ethanol.
Samples for RP-HPLC analysis were diluted with 2 M acetic acid prior to analysis.

| Sample | Identification | M13 conc. | Volume | Amount | % |
|---|---|---|---|---|---|
| Application | E127b | 0.35 mg/ml | 120 ml | 42.0 mg | 100 |
| Run through | E127c | 0.00 mg/ml | | 0.0 mg | 0 |
| Wash | E127d | 0.00 mg/ml | | 0.0 mg | 0 |
| Fraction 3 | E127e | 2.26 mg/ml | 5.0 ml | 11.3 mg | 0 |
| Fraction 4 | E127f | 2.07 mg/ml | 5.0 ml | 10.4 mg | |
| Fraction 5 | E127g | 1.12 mg/ml | 5.0 ml | 5.6 mg | |
| Fraction 6 | E127h | 1.27 mg/ml | 5.0 ml | 6.4 mg | |
| Fractions | | | | 33.6 mg | 79% |

Thus a total recovery of 79% was obtained.
The purity of the product was determined to 93% by RP-HPLC analysis. The remaining impurities were insulin related.

EXAMPLE 135

Purification of [Asp$^{B28}$]-insulin-B-chain$^{1-29}$-A-A-K-insulin-A-chain$^{1-21}$ on an affinity ligand-matrix conjugate according to Example 171:

Centrifuged broth (batch GSG9414) was adjusted to pH 5.5 with 5 M NaOH and filtered through a Leitz Tiefenfilter (Seitz EK) filter followed by filtration through a Leitz Tiefenfilter (Seitz EKS) filter. The concentration was measured to 0.02 mg/ml by RP-HPLC. The ionic strength was measured to 17.0 mS/cm and the redox potential to 308 mV.

800 ml of the above solution was applied a Pharmacia K16 (1.6×6 cm) column packed with 12 ml of the above matrix conjugate, equilibrated in 0.2 M potassium citrate pH 5.5, at 1.8 ml/min at ambient temperature. The column was washed in 50 ml of 0.2 M potassium citrate pH 5.5 and then eluted with 0.1 M acetic acid at 1.8 ml/min. 12 fractions of 5.0 ml were collected.

The column was cleaned with 50 ml of 0.5 M NaOH and regenerated with 50 ml of 0.1 M citric acid, 60% v/v ethanol.
Samples for RP-HPLC analysis were diluted with 2 M acetic acid prior to analysis.

| Sample | Identification | M13 conc. | Volume | Amount | % |
|---|---|---|---|---|---|
| Application | E107b | 0.02 mg/ml | 800 ml | 16.0 mg | 100 |
| Run through | E107c | 0.00 mg/ml | | 0.0 mg | 0 |
| Wash | E107d | 0.00 mg/ml | | 0.0 mg | 0 |
| Fraction 2 | E109a | 0.00 mg/ml | 5.0 ml | 0.0 mg | 0 |
| Fraction 3 | E109b | 0.12 mg/ml | 5.0 ml | 0.6 mg | |
| Fraction 4 | E109c | 0.76 mg/ml | 5.0 ml | 3.8 mg | |
| Fraction 5 | E109d | 1.04 mg/ml | 5.0 ml | 5.2 mg | |
| Fraction 6 | E109e | 0.31 mg/ml | 5.0 ml | 1.6 mg | |
| Fraction 7 | E109f | 0.10 mg/ml | 5.0 ml | 0.5 mg | |
| Fraction 8 | E109g | 0.06 mg/ml | 5.0 ml | 0.3 mg | |
| Fractions | | | | 12 mg | 75% |

Thus a total recovery of 75% was obtained.
The purity of the product was determined to 84% by RP-HPLC analysis. The remaining impurities were insulin related.

EXAMPLE 136

This example further demonstrates the screening process by which the protein binding properties of affinity ligand-matrix conjugates of this invention may be identified.

A library of affinity ligand matrix conjugates of this invention were synthesised according to example 74 except that the 5 mole equivalents of the amine compound listed in Column II of Table 4 were replaced by the corresponding amount of the amine compound listed in Column II of Table 5 and the mole equivalents of the amine compound listed in Column III of Table 4 were replaced by the corresponding amount of the amine compound listed in Column III of Table 5. A library of affinity ligand-matrix conjugates of this invention was synthesised, Examples of which are identified in Column I of Table 5.

Chromatography columns of 1 ml total volume were packed with affinity ligand-matrix conjugates of Examples 137–180. The columns were equilibrated by flushing with 10 ml of 0.2 M sodium acetate, 0.1 M sodium chloride buffer, pH 5.0. Twelve ml of clarified fermenter broth containing 50 mg/ml human insulin precursor was applied to each chromatography column which were subsequently washed with 12 ml of 0.2 M sodium acetate, 0.1 M sodium chloride buffer, pH 5.0 to remove non-bound material. Bound human insulin precursor was eluted by flushing each column with 3 ml of 2M acetic acid. The human insulin precursor content of the flow-through, wash and elution fractions was determined by high performance liquid chromatography (HPLC) using a C18 reverse-phase silica column (4×250 mm) and a solvent system comprising buffer A (0.2 M sodium sulphate, 40 mM phosphoric acid and 10% (v/v) acetonitrile, pH 2) and buffer B (50% (v/v acetonitrile) delivered at a flow rate of 1 ml per minute in the proportions 55% buffer A to 45% buffer B. The elution time of human insulin precursor was determined by comparison to a reference standard.

Analysis of the results revealed affinity ligand-matrix conjugates of Examples 139, 140, 145, 148, 153, 159, 162, 163, 164, 166, 167, 170, 171, 173 all bound human insulin precursor which was eluted under the conditions described in this Example. As a consequence, affinity ligand-matrix conjugates of Examples 139, 140, 145, 148, 153, 159, 162, 163, 164, 166, 167, 170, 171, 173 are considered to be of execeptional value in the separation, isolation or purification of human insulin precursor.

TABLE 5

| I | II | III |
|---|---|---|
| 137 | 1-amino-6-naphthalenesulphonic acid | benzylamine |
| 138 | 1-amino-6-naphthalenesulphonic acid | 3,5-diaminobenzoic acid |
| 139 | 1-amino-5-naphthol | benzylamine |
| 140 | 1-amino-5-naphthol | 3,5-diaminobenzoic acid |
| 141 | benzylamine | 3-aminobenzoic acid |
| 142 | benzylamine | 4-aminobenzoic acid |
| 143 | tyramine | 3-aminobenzoic acid |
| 144 | tyramine | 4-aminobenzoic acid |
| 145 | 1-amino-5-naphthol | 1-amino-5-naphthol |
| 146 | 1-amino-5-naphthol | 3-aminobenzoic acid |
| 147 | 1-amino-5-naphthol | 4-aminobenzoic acid |
| 148 | 1-amino-5-naphthol | tyramine |
| 149 | 1-amino-6-naphthalenesulphonic acid | tyramine |
| 150 | 1-amino-5-naphthol | 3-amino-1,2-propanediol |
| 151 | 1-amino-5-naphthol | 3-aminopropan-1-ol |
| 152 | 1-amino-5-naphthol | 5-aminopentan-1-ol |
| 153 | 1-amino-5-naphthol | 3-aminophenol |
| 154 | 1-amino-5-naphthol | 6-aminocaproic acid |
| 155 | 1-aminonaphthalene | benzylamine |
| 156 | 1-aminonaphthalene | 3,5-diaminobenzoic acid |
| 157 | 1-aminonaphthalene | 3-aminobenzoic acid |
| 158 | 1-aminonaphthalene | 4-aminobenzoic acid |
| 159 | 3-amino-2-naphthoic acid | 3-aminophenol |
| 160 | 4-amino-1-naphthol | 3-aminophenol |

TABLE 5-continued

| I | II | III |
|---|---|---|
| 161 | 1-amino-2-naphthol | 3-aminophenol |
| 162 | 3-amino-2-naphthol | 3-aminophenol |
| 163 | 1-amino-6-naphthol | 3-aminophenol |
| 164 | 1-amino-7-naphthol | 3-aminophenol |
| 165 | 2-amino-1-naphthol | 3-aminophenol |
| 166 | 6-amino-1-naphthol | 3-aminophenol |
| 167 | 3-amino-2-naphthoic acid | 3-amino-2-naphthoic acid |
| 168 | 4-amino-1-naphthol | 4-amino-1-naphthol |
| 169 | 1-amino-2-naphthol | 1-amino-2-naphthol |
| 170 | 3-amino-2-naphthol | 3-amino-2-naphthol |
| 171 | 1-amino-7-naphthol | 1-amino-7-naphthol |
| 172 | 2-amino-1-naphthol | 2-amino-1-naphthol |
| 173 | 6-amino-1-naphthol | 6-amino-1-naphthoi |
| 174 | 3-amino-2-naphtoic acid | 1-amino-5-naphthol |
| 175 | 3-amino-2-naphthoic acid | 4-amino-1-naphthol |
| 176 | 3-amino-2-naphthoic acid | 2-amino-1-naphthol |
| 177 | 1-amino-7-naphthol | 1-amino-5-naphthol |
| 178 | 1-amino-7-naphthol | 3-amino-2-naphthoic acid |
| 179 | 1-amino-7-naphthol | 4-amino-1-naphthol |
| 180 | 1-amino-7-naphthol | 2-amino-1-naphthol |

EXAMPLE 181

This example demonstrates the process by which affinity ligand-matrix conjugates of this invention may be synthesised which are of value for the purification of Factor VII.

An affinity ligand-matrix conjugate of this invention was synthesised according to Example 74 except that the 5 mole equivalents of the amine compound listed in Column II of Table 4 were replaced by the corresponding amount of 2-aminobenzimidazole and the 5 mole equivalents of the amine compound listed in Column III of Table 4 were replaced by 3-amino-2-naphthoic acid. This affinity ligand-matrix conjugate may be used for the purification of Factor VIIa according to Example 129 of this invention.

EXAMPLE 182

Purification of EEAEPK-insulin B-chain$^{1-29}$-A-A-K-insulin A-chain$^{1-21}$ on an affinity ligand-matrix conjugate according to Example 171:

50 ml of ionexchange purified insulin precursor (EEAEPK-insulin B-chain$^{1-29}$-A-A-K-insulin A-chain$^{1-21}$ at 2.2 mg/ml) was applied a Pharmacia K16 (1.6×6 cm) column packed with 12 ml of the conjugate matrix, equilibrated in 0.2 M potassium citrate pH 5.5, at 1.8 ml/min at ambient temperature. The column was washed in 50 ml of 0.1 M potassium citrate, 0.2 M potassium sulfate pH 5.5 and then eluted with 0.1 M acetic acid at 1.8 ml/min. 5.0 ml fractions were collected.

The column was cleaned with 50 ml of 0.5 M NaOH and regenerated with 50 ml of 0.1 M citric acid, 60% v/v ethanol.

Samples for RP-HPLC analysis were diluted with 2 M acetic acid prior to analysis.

| Sample | Identification | Conc. mg/ml | Volume ml | Amount mg | % |
|---|---|---|---|---|---|
| Application | R-029e | 2.27 | 50 | 114 | 100 |
| Run through | R-033a | 0.03 | 50 | 1.4 | 1.2 |
| Wash | R-033b | 0.09 | 50 | 4.3 | 3.8 |
| Pool 1 | R-033c | 5.61 | 15 | 84.2 | 74 |
| Pool 2 | R-033d | 0.55 | 10 | 5.5 | 4.8 |

A dynamic binding capacity of 9.5 mg/ml matrix was demonstrated with a yield of 88% of the precursor.

EXAMPLE 183

This example illustrates the synthesis of a library of affinity ligand-matrix conjugates of this invention which may be subsequently screened to determine their Factor VII binding properties.

One part of agarose bearing amino groups was mixed with 1 part 1 M potassium phosphate buffer, pH 7.0 and settled under gravity. The buffered amine agarose was transferred to a reaction vessel and mixed at 0–5° C. with 0.5 parts 0.5M potassium phosphate buffer, pH 7.0 and 0.5 parts acetone. One quarter of a part of a solution comprising 1 part cyanuric chloride in 10 parts acetone was added and the mixture stirred at 0–5° C. for 1 hour, after which the mixture was filtered and washed sequentially with 10 parts 50% acetone, 6 parts water, 6 parts 50% acetone and 10 parts water to provide 2,4-dichloro-s-triazin-6-yl activated agarose.

One part of the 2,4-dichloro-s-triazin-6-yl activated agarose was added to 5 mole equivalents of the amine compound listed in Column II of Table 5 dissolved in 2 to 3 parts of a solution comprising 1 part acetone and 1 part water and adjusted to neutral pH by addidtion of sodium hydroxide. The suspension was mixed for 24 hours at 30° C. The resulting monochloro-s-triazin-6-yl activated agaroses were washed sequentially with 10 parts of dimethylformamide, 10 parts of a solution comprising 3 parts propan-2-ol and 7 parts 0.2M sodium hydroxide, 10 parts of water and settled under gravity.

One part of the monochloro-s-triazin-6-yl-activated agarose was added to 5 mole equivalents of the amine compound listed in Column III of Table 5 dissolved in 2 to 3 parts of a solution comprising 1 part dimethylformamide and 1 part water and adjusted to neutral pH by addition of sodium hydroxide. The suspension was mixed for 72 hours at 85 to 95° C. The resulting affinity ligand-matrix conjugates were washed sequentially with 10 parts of dimethylformamide, 10 parts of a solution comprising 3 parts propan-2-ol and 7 parts 0.2M sodium hydroxide, 10 parts of water and settled under gravity.

A library of affinity ligand-matrix conjugates of this invention was synthesised, Examples of which are identified in Column I of Table 5.

TABLE 5

| I | II | III |
|---|---|---|
| 184 | 1-amino-5-naphthol | 4-aminobenzoic acid |
| 185 | 4-aminobenzamidine | 3-amino-2-naphthoic acid |
| 186 | 2-aminobenzimidazole | 3-amino-2-naphthoic acid |
| 187 | 2-amino-5,6-dimethylbenzimidazole | 3-amino phenol |
| 188 | 5-aminoindan | 6-aminoindazole |
| 189 | 3-amino-2-naphthoic acid | 3-amino-2-naphthoic acid |
| 190 | 2-amino-6,8-dihydroxypurin | 3-amino-2-naphthoic acid |
| 191 | 2-aminobenzimidazole | 3-aminobenzoic acid |
| 192 | 3-amino-2-naphthoic acid | 2-aminophenol |
| 193 | 5-amino-3-methyl-1-phenypyrazole | 3-aminobenzoic acid |
| 194 | 2-aminobenzimidazole | 2-aminophenol |

EXAMPLE 195

This example demonstrates the screening process by which the Factor VII binding properties of affinity ligand-matrix conjugates described in Example 183 may be identified.

Chromatography columns of 1 ml total volume (Pharmacia HR 5/5 columns) were packed with affinity ligand-matrix conjugates of Examples 184–194. The columns were equilibrated by flushing with 20 ml of a buffer comprising 20 mM Tris-HCl, 50 mM NaCl, 5 mM CaCl$_2$, pH 8.0. 3 ml of a solution comprising 1.5 mg of pure Factor VIIa, 20 mM Tris-HCl, 50 mM NaCl, 5 mM CaCl2, pH 8.0 was applied to each chromatography column which were subsequently washed with 10 ml of 20 mM Tris-HCl, 50 mM NaCl, 5 mM CaCl$_2$, pH 8.0 to remove non-bound Factor VIIa. Bound Factor VIIa was eluted by flushing each column with 5 ml of a solution comprising 50 mM Tris-HCl, 20 mM tri-sodium citrate, pH 8.0. The columns were regenerated by flushing with 5 ml of a solution comprising 30% isopropanol and 0.2 M NaOH and in this way remaining Factor VIIa bound to the column was released. The chromatographic procedure was carried out at ambient temperature and the flow rate was 0.3 ml/min. The relative Factor VIIa content of the flowthrough/wash, elution and regeneration fraction was determined by integration of the UV-curve (measurement of absorbance at 280 nm). Analysis of the results revealed affinity ligand-matrix conjugates of Example 186, 188, 189, 190, 191, 192, 193 all exhibited Factor VIIa binding. The majority of the applied amount of Factor VIIa was eluted with the solution comprising 50 mM Tris-HCl, 20 mM tri-sodium citrate, pH 8.0 in Examples 186, 190, 191, 192 and 193. As a consequence the affinity ligand-matrix conjugates of Examples 186, 190, 191, 192 and 193 are considered to be of exceptional value in the separation, isolation or purification of Factor VIIa.

EXAMPLE 196

A library of affinity ligand-matrix conjugates of this invention was synthesised, Examples of which are identified in Column I of Table 6.

TABLE 6

| I | II | III |
|---|---|---|
| 197 | U | 3-amino-2-naphthoic acid | 5-amino-3-methyl-1-phenypyrazole |
| 198 | U | 4-aminobenzoic acid | 2-aminobenzimidazole |
| 199 | U | 3-aminobenzoic acid | 3-aminobenzoic acid |
| 200 | U | 3-amino-2-naphthoic acid | 2-aminobenzimidazole |
| 201 | U | 3-amino-2-naphthoic acid | 2-aminophenol |

EXAMPLE 202

This example demonstrates the screening process by which the Factor VII binding properties of affinity ligand-matrix conjugates described in Example 196 may be identified.

Chromatography columns of 1 ml total volume were packed with affinity ligand-matrix conjugates of Examples 197–201. The columns were equilibrated by flushing with 20 ml of a buffer comprising 20 mM Tris-HCl, 50 mM NaCl, 5 mM CaCl$_2$, pH 8.0. 3 ml of a solution comprising 1.5 mg of pure Factor VIIa, 20 mM Tris-HCl, 50 mM NaCl, 5 mM CaCl2, pH 8.0 was applied to each chromatography column which were subsequently washed with 10 ml of 20 mM Tris-HCl, 50 mM NaCl, 5 mM CaCl2, pH 8.0 to remove non-bound Factor VIIa. Bound Factor VIIa was eluted by flushing each column with 5 ml of a solution comprising 50 mM Tris-HCl, 20 mM tri-sodium citrate, pH 8.0. The columns were regenerated by flushing with 5 ml of a solution comprising 30% isopropanol and 0.2 M NaOH and in this way remaining Factor VIIa bound to the column was released. The chromatographic procedure was carried out at ambient temperature and the flow rate was 0.3 ml/min. The relative Factor VIIa content of the flowthrough/wash, elution and regeneration fraction was determined by integration of the UV-curve (measurement of absorbance at 280 nm). Analysis of the results revealed affinity ligand-matrix conjugates of Example 197, 198, 199, 200 and 201 all exhibited Factor VIIa binding. The majority of the applied amount of Factor VIIa was eluted with the solution comprising 50 mM Tris-HCl, 20 mM tri-sodium citrate, pH 8.0 in Examples 197, 198, 199, 200 and 201. In Example 198 43% of the applied amount of Factor VIIa was eluted. As a consequence the affinity ligand-matrix conjugates of Examples 197, 198, 199, 200 and 201 are considered to be of exceptional value in the separation, isolation or purification of Factor VIIa.

EXAMPLE 203

This example illustrates the dependency of the binding properties of Factor VIIa on the ionic strength, given by the concentration of NaCl during the application phase and during the washing phase. Example 195 was repeated but using only affinity ligand-matrix conjugate of Example 192 and replacing the 50 mM concentration of NaCl in the equilibration buffer and in the applied solution and in the washing buffer with the concentration of NaCl given in the first column of Table 7. The relative Factor VIIa content of the flowthrough/wash, elution and regeneration fraction obtained is given in Table 7 for each concentration of NaCl. In all cases the majority of the applied amount of Factor VIIa was eluted with the solution comprising 50 mM Tris-HCl, 20 mM tri-sodium citrate, pH 8.0.

This demonstrates that the binding of Factor VIIa to the affinity ligand-matrix conjugate sample 192 is relatively insensitive to the ionic strength (given by the concentration of NaCl).

TABLE 7

| Concentration of NaCl in mM | Relative content of Factor VIIa in % | | |
|---|---|---|---|
| | Flowthrough/wash | Elution | Regeneration |
| 50 | 0.0 | 78.5 | 21.5 |
| 100 | 2.3 | 79.7 | 18.0 |
| 150 | 5.6 | 73.8 | 20.6 |
| 200 | 7.3 | 72.0 | 20.7 |
| 300 | 29.3 | 56.8 | 13.9 |
| 500 | 36.6 | 50.3 | 13.1 |
| 1000 | 24.5 | 62.4 | 13.1 |
| 2000 | 0.3 | 84.3 | 15.4 |

EXAMPLE 204

This example demonstrates the selectivity that can be obtained with the use of the affinity ligand-matrix conjugates in the purification of Factor VIIa.

Chromatography columns of 1 ml total volume (Pharmacia HR 5/5 columns) were packed with affinity ligand-matrix conjugates of Examples 191, 199, 200 and 201. The columns were equilibrated by flushing with 20 ml of a buffer comprising 20 mM Tris-HCl, 50 mM NaCl, 5 mM CaCl2, pH 8.0. Eluate from the first ionex-change column in the purification process of Factor VIIa was adjusted to a NaCl concentration of 100 mM and pH 8.0. The eluate was 87% pure as measured by RP-HPLC. An adjusted eluate volume corresponding to 1.5 mg Factor VIIa was applied to each chromatography column with the affinity ligand-matrix conjugates mentioned above. The columns were subsequently washed with 10 ml of 20 mM Tris-HCl, 50 mM NaCl, 5 mM CaCl2, pH 8.0 to remove non-bound Factor VIIa. Bound Factor VIIa was eluted by flushing each column with 5 ml of a solution comprising 50 mM Tris-HCl, 20 mM tri-sodium citrate, pH 8.0. The columns were regenerated by flushing with 5 ml of a solution comprising 30% isopropanol and 0.2 M NaOH and in this way remaining Factor VIIa bound to the column was released. The chromatographic procedure was carried out at ambient temperature and the flow rate was 0.3 ml/min The purity and the Factor VIIa content of the elution fraction relative to the applied amount were determined by RP-HPLC. The results revealed that the purity of the elution fraction was 99% or higher with affinity ligand-matrix conjugates of Examples 191, 199, 200 and 201. The Factor VIIa content of the elution fraction relative to the applied amount was between 42% and 76%. This demonstrates that the affinity ligand-matrix conjugates of Examples 191, 199, 200 and 201 are highly specific and selective with respect to the purification of Factor VIIa from a mixture containing protein contaminants.

What is claimed is:

1. Affinity ligand-matrix conjugates comprising a ligand with the general formula (a):

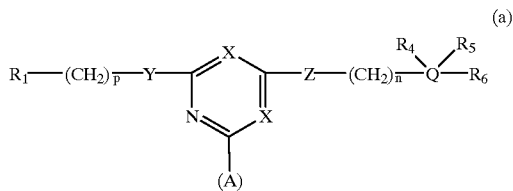

wherein $R_1$ represents a hydrogen atom, an alkyl group containing from 1 to 6 carbon atoms, a hydroxyalkyl group containing from 1 to 6 carbon atoms, a cyclohexyl group, an amino group, a phenyl group, naphthyl group, 1-phenylpyrazole, indazole, benzthiazole group, benzoxazole group or a benzimidazole group, each of which benzene, naphthalene, 1-phenylpyrazole, indazole, benzthiazole, benzoxazole or benzimidazole ring is optionally substituted with one or more substituents independently selected from the group consisting of alkyl groups containing from 1 to 6 carbon atoms, alkoxy groups containing from 1 to 6 carbon atoms, acyloxy or acylamino groups containing from 1 to 6 carbon atoms, amino groups, hydroxyl groups, carboxylic acid groups, sulphonic acid groups, carbamoyl groups, sulphamoyl groups, alkylsulphonyl groups containing from 1 to 6 carbon atoms and halogen atoms;

Y represents an oxygen atom, a sulphur atom or a group N—$R_2$;

Z represents an oxygen atom, a sulphur atom or a group N—$R_3$;

$R_2$ and $R_3$ each independently represent a hydrogen atom, an alkyl group containing from 1 to 6 carbon atoms; a hydroxyalkyl group containing from 1 to 6 carbon atoms, a benzyl group or a β-phenylethyl group;

$R_4$, $R_5$ and $R_6$ each independently represent a hydrogen atom, a hydroxyl group, an alkyl group containing from 1 to 6 carbon atoms, an alkoxy group containing from 1 to 6 carbon atoms, an amino group, an acyloxy or acylamino group containing from 1 to 6 carbon atoms, a carboxylic acid group, a sulphonic acid group, a carbamoyl or sulphamoyl group, an alkylsulphonyl group containing from 1 to 6 carbon atoms or a halogen atom;

X represents a nitrogen atom one of the symbols represents a nitrogen atom and the other symbol Q represents a benzene, naphthalene, 1-phenylpyrazole, indazole, benzthiazole, benzoxazole or benzimidazole ring;

n is an integer between 0 and 6;

p is an integer between 0 and 20; and which ligand is attached to a support matrix in position (A), optionally through a spacer arm interposed between the matrix and ligand.

2. Affinity ligand-matrix conjugates according to claim 1 wherein the optional spacer arm interposed between the ligand and the matrix is represented by the general formula (b)

$$-T-[-L-V-]_m-\qquad (b)$$

wherein T represents an oxygen atom, a sulphur atom or a group N—$R_7$;

wherein $R_7$ represents a hydrogen atom or an alkyl group containing from 1 to 6 carbon atoms;

V represents an oxygen atom, a sulphur atom, a —COO— group, a CONH group or an NHCO group or a —$PO_3H$— group, an NH-arylene-$SO_2$—$CH_2$—$CH_2$ group or an N—$R_8$ group; wherein $R_8$ represents a hydrogen atom or an alkyl group containing from 1 to 6 carbon atoms;

L represents an optionally substituted hydrocarbon linkage containing from 2 to 20 carbon atoms; and m is 0 or 1.

3. Affinity ligand-matrix conjugates which are represented by the General Formula (I):

$$R_1-(CH_2)_p-Y-\underset{\underset{T-[L-V-]_m M}{\overset{X}{\bigvee}}}{\overset{X}{\bigvee}}-Z-(CH_2)_n-Q\overset{R_4\ R_5}{\underset{R_6}{\bigvee}} \qquad (I)$$

wherein $R_1$, Y, Z, $R_2$, $R_3$, $R_4$, $R_5$, $R_6$, X, Q, n and p are as defined above T represents an oxygen atom, a sulphur atom or a group N—$R_7$;

V represents an oxygen atom, a sulphur atom, a —COO— group, a CONH group or an NHCO group or a —$PO_3H$— group, an NH-arylene-$SO_2$—$CH_2$—$CH_2$ group or an N—$R_8$ group;

$R_7$ and $R_8$ each independently represents a hydrogen atom or an alkyl group containing from 1 to 6 carbon atoms;

L represents an optionally substituted hydrocarbon linkage containing from 2 to 20 carbon atoms;

m is 0 or 1; and

M represents the residue of a support matrix.

4. Affinity ligand matrix conjugates according to claim 1 wherein M represents the residue of a support matrix which may be any compound or material, particulate or non particulate, soluble or insoluble, porous or non-porous which may be used in conjunction with affinity ligands to form a novel affinity ligand-matrix conjugate according to anyone of the preceding claims and which provides a convenient means of separating the affinity ligands from solutes in a contacting solution.

5. Affinity ligand-matrix conjugates according to claim 1 wherein $R_1$ represents a phenyl or naphthyl group each of which is optionally substituted on the benzene or naphthalene ring with one or more independently selected from hydroxyl groups and carboxylic acid groups.

6. Affinity ligand-matrix conjugates according to claim 1 claims wherein $R_2$ represents a hydrogen atom.

7. Affinity ligand-matrix conjugates according to claim 1 wherein $R_3$ represents a hydrogen atom.

8. Affinity ligand-matrix conjugates according to claim 1 wherein $R_4$ represents a hydrogen atom, a hydroxyl group, a carboxylic acid group, or an amino group.

9. Affinity ligand-matrix conjugates according to claim 1 wherein $R_5$ represents a hydrogen atom, a hydroxyl group, a carboxylic acid group, or an amino group.

10. Affinity ligand-matrix conjugates according to claim 1 wherein $R_6$ represents a hydrogen atom, a hydroxyl group, a carboxylic acid group, or an amino group.

11. Affinity ligand-matrix conjugates according to claim 1 wherein $R_7$ represents a hydrogen atom.

12. Affinity ligand-matrix conjugates according to claim 1 wherein T represents an oxygen atom or an NH group.

13. Affinity ligand-matrix conjugates according to claim 1 wherein Y represents N—$R_2$ wherein $R_2$ is as defined above.

14. Affinity ligand-matrix conjugates according to claim 1 wherein Z represents N—$R_3$ wherein $R_3$ is as defined above.

15. Affinity ligand-matrix conjugates according to claim 1 wherein Q represents a benzene or naphthalene ring.

16. Affinity ligand-matrix conjugates according to claim 1 wherein n represents 0 or 2.

17. Affinity ligand-matrix conjugates according to claim 1 wherein p represents 0 or 2.

18. Affinity ligand-matrix conjugates according to claim 1 wherein m represents 0 or 1.

19. Affinity ligand-matrix conjugates according to claim 1 claims wherein L represents an ethyl, propyl, hydroxy propyl, butyl, pentyl, hexyl, octyl or decyl group and V and m are as defined above.

20. An affinity ligand-matrix conjugate according to claim 1 wherein V represents an oxygen atom or an NH group and L and m are as defined above.

21. Affinity ligand-matrix conjugates according to claim 1 wherein m represents 1 and L and V are as defined above.

22. Affinity ligand-matrix conjugates according to claim 1 wherein the residue of a support matrix M represents optionally activated agarose, silica, cellulose, glass, toyopearl, hydroxyethylmethacrylate, polyacrylamide, styrenedivinylbenzene, Hyper D, perfluorocarbons.

23. Affinity ligand-matrix conjugates according to claim 22 wherein M represents optionally tresyl activated, sulphonylchloride activated, tosyl activated, vinylsulphone activated or epoxy activated agarose.

24. Affinity ligand-matrix conjugates according to claim 1 selected from:

i)

[Structure: triazine with phenyl-NH, NH-(CH$_2$)$_2$-phenyl-OH, and NH-(CH$_2$)$_2$-NH-M substituents]

-continued ii) 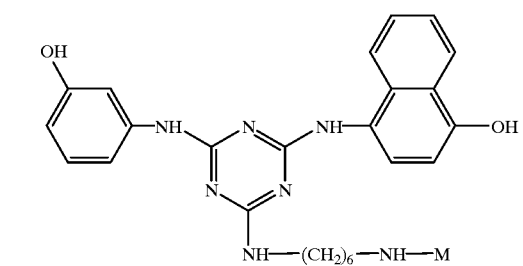

iii) 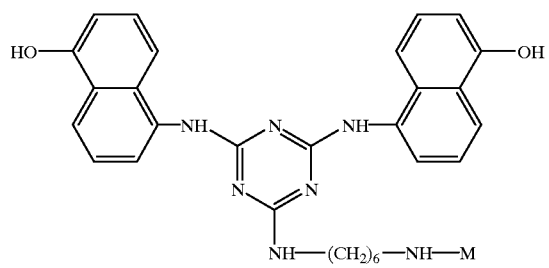

iv) 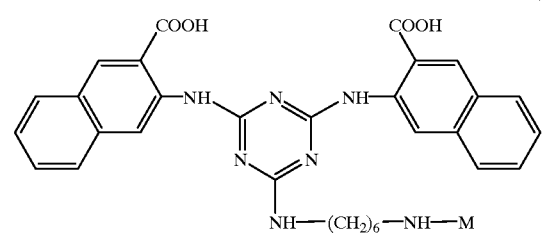

v) 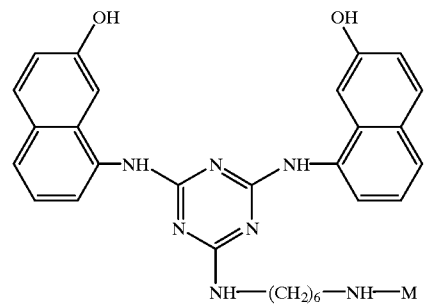

vi) 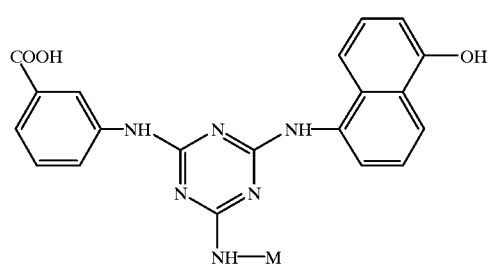

-continued vii) 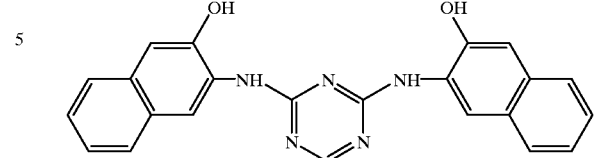

viii) 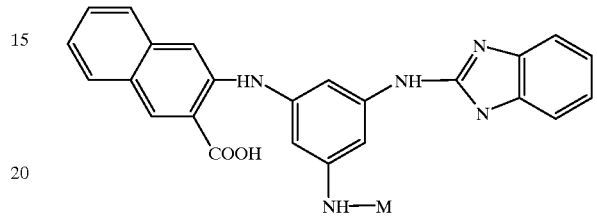

wherein M is as defined above.

25. A method for the manufacture of the affinity ligand-matrix conjugates as defined in claim 1 which comprises reacting, in any order, a halogenoheterocylic compound of formula (II):

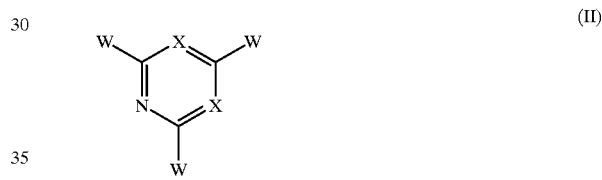 (II)

wherein X represents a nitrogen atom and W represents a halogen atom with (i) a compound of formula (III):

 (III)

wherein the symbols $R_1$, p and Y have the meanings as defined in claim 1, (ii) a compound of formula (IV)

 (IV)

wherein the symbols $R_4$, $R_5$, $R_6$, Q, Z and n have the meanings as defined in claim 1, and (iii) an optionally derivatized support matrix of formula V

 (V)

wherein the symbols L, M, V, T, and m have the meanings as defined in claim 3.

26. A method for the manufacture of the affinity ligand-matrix conjugates as defined in claim 1 which comprises reacting, in any order, a halogenoheterocyclic compound of formula (II), as defined in claim 25, with (i) a compound of formula (III), as defined in claim 25

(ii) a compound of formula (IV), as defined in claim 25 and (iii) with a linking unit of formula (VI)

H—T—L—V—H (VI)

wherein the symbols L, V and T have the meanings as defined in claim 3 to give a compound of formula (VII):

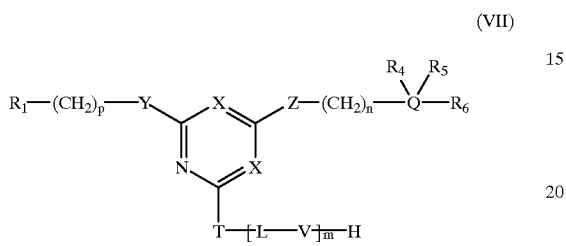

(VII)

wherein R, $R_4$, $R_5$, $R_6$, T, Q, L, V, X, Y, Z, m, n and p have the meanings as defined in claim 3, followed by reaction of the compound of formula (VII) with a matrix support.

27. Affinity ligands of formula (XII):

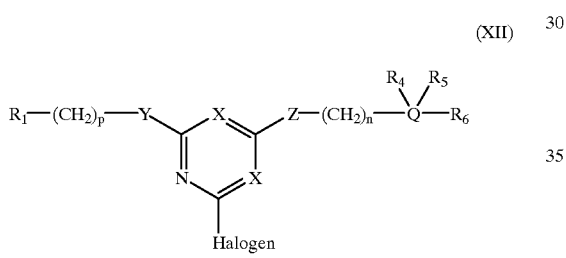

(XII)

wherein R, $R_4$, $R_5$, $R_6$, Q, X, Y, Z, n and p have the meanings as defined in claim 1 and Halogen represents a fluorine, chlorine, bromine or iodine atom.

28. A method of attaching the affinity ligands of formula (XII), as claimed in claim 27, to a matrix of formula (V), as defined in claim 25, by reacting the affinity ligands with the matrix at temperatures between $-20°$ C. and $121°$ C., optionally in the presence of an acid binding agent.

29. Affinity ligands of formula (XIII):

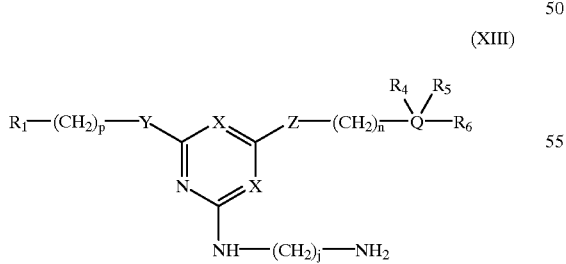

(XIII)

wherein R, $R_4$, $R_5$, $R_6$, Q, X, Y, Z, n and p have the meanings as defined in claim 1 and j is an integer between 2 and 20.

30. A method of preparing affinity ligands of formula (XIII), as claimed in claim 29, by reacting a compound of formula (XII), as claimed in claim 27, with an alkylene diamine of formula $H_2N-(CH_2)_j-NH_2$ at temperatures between $0°$ C. and $100°$ C. in the presence of an acid binding agent.

31. Affinity ligands according to claim 27 selected among the following:

(1)

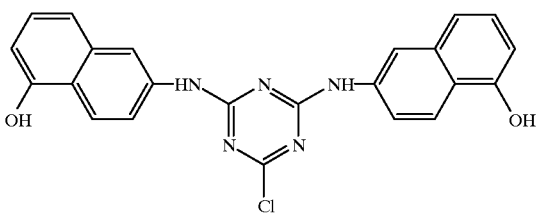

(2)

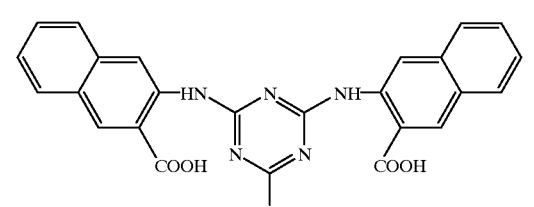

(3)

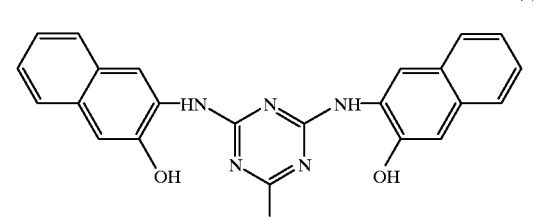

(4)

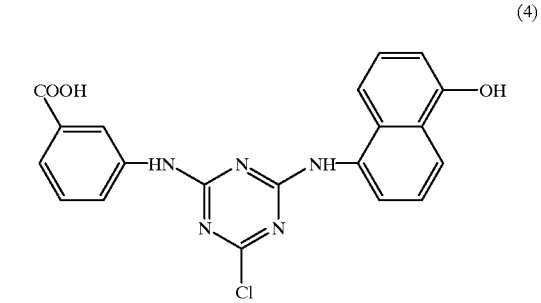

(5)

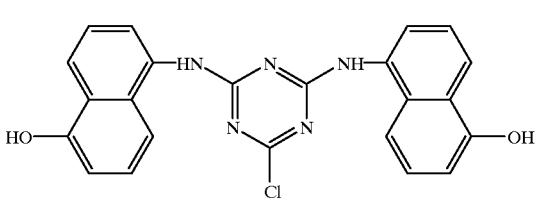

(6)

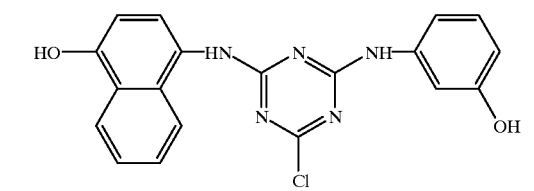

-continued (7)
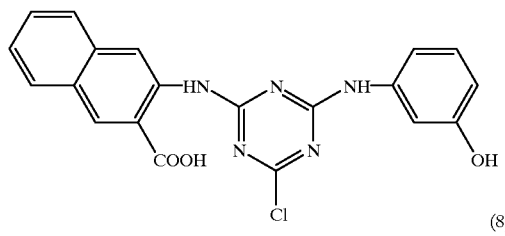

(8)
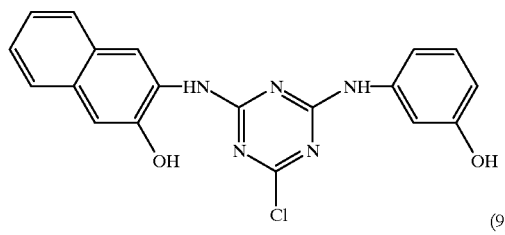

(9)
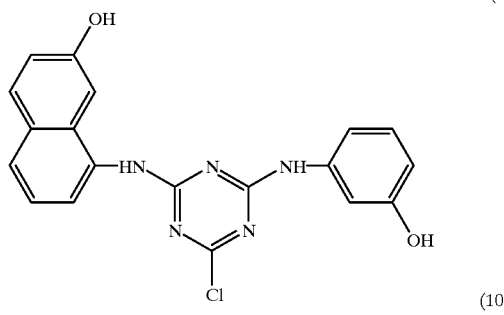

(10)
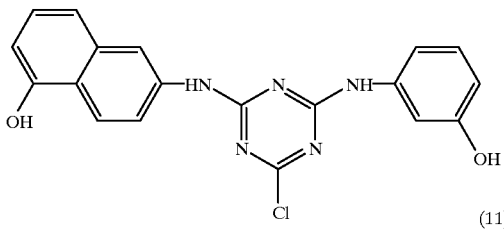

(11)
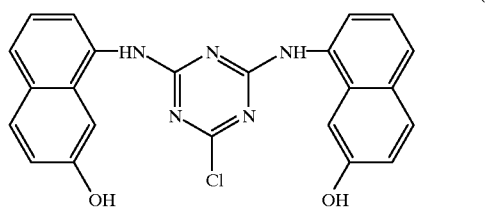

-continued

(12)
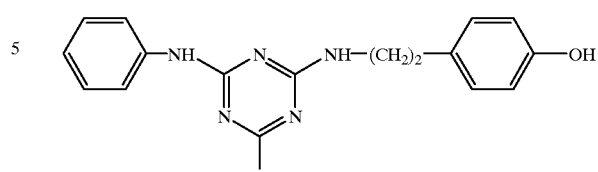

(13)
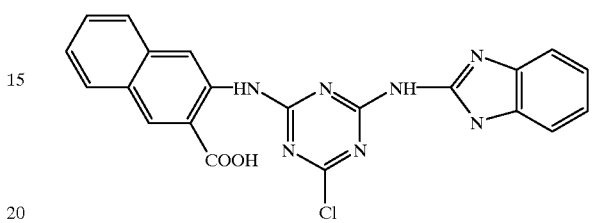

32. A process for the separation or purification of proteinaceous materials comprising carrying out affinity chromatography using as the biospecific ligand a ligand of formula (a) as defined in claim 1.

33. The separation, isolation, purification, characterization, identification or quantification of proteins by any process whereby said proteins are applied to the affinity ligand-matrix conjugates of claim 1, and subsequently removed, eluted or desorbed.

34. The separation, isolation, purification, characterization, identification or quantification of the proteins of claim 33 wherein the proteins are immunoglobulins or subclasses, fragments, precursors or derivatives thereof, whether derived from natural or recombinant sources.

35. The separation, isolation, purification, characterization, identification or quantification of the proteins of claim 33 wherein the proteins are insulins or insulin analogues, derivatives and fragments thereof and precursors, whether derived from natural or recombinant sources.

36. The separation, isolation, purification, characterization, identification or quantification of the proteins of claim 33 wherein the protein is Factor VII or analogues, derivatives and fragments thereof and precursors, whether derived from natural or recombinant sources.

* * * * *

UNITED STATES PATENT AND TRADEMARK OFFICE

CERTIFICATE OF CORRECTION

PATENT NO. : 6,117,996

DATED : September 12, 2000

INVENTOR(S) : Lowe et al.

It is certified that error appears in the above-identified patent and that said Letters Patent is hereby corrected as shown below:

Title page, bracket number [73] Assignee: change "Novo Nordisk A/S, Bagsvaerd, Denmark" to --[73] Assignee: Novo Nordisk A/S, Bagsvaerd, Denmark and Prometic Biosciences Limited, Freeport, Ballasalla Isle of Man IM9 2AP, United Kingdom--

Signed and Sealed this

Twenty-fourth Day of April, 2001

*Attest:*

NICHOLAS P. GODICI

*Attesting Officer*     Acting Director of the United States Patent and Trademark Office